(12) United States Patent
Dumas et al.

(10) Patent No.: US 7,879,592 B2
(45) Date of Patent: Feb. 1, 2011

(54) MODIFIED YEASTS AND USES THEREOF, IN PARTICULAR FOR PRODUCING STEROID DERIVATIVES

(75) Inventors: Bruno Dumas, Massy (FR); Gilles Cauet, Griesheim/Souffel (FR); Tilman Achstetter, Bremen (DE); Eric Degryse, Crosne (FR)

(73) Assignee: Aventis Pharma S.A., Antony (FR)

( * ) Notice: Subject to any disclaimer, the term of this patent is extended or adjusted under 35 U.S.C. 154(b) by 804 days.

(21) Appl. No.: 10/343,993

(22) PCT Filed: Jul. 24, 2001

(86) PCT No.: PCT/FR01/02417

§ 371 (c)(1),
(2), (4) Date: Oct. 21, 2003

(87) PCT Pub. No.: WO02/12536

PCT Pub. Date: Feb. 14, 2002

(65) Prior Publication Data

US 2004/0082025 A1    Apr. 29, 2004

(30) Foreign Application Priority Data

Aug. 8, 2000    (FR) .................................. 00 10437

(51) Int. Cl.
*C12N 1/14* (2006.01)
*C12N 1/20* (2006.01)
*C12N 9/04* (2006.01)
*C12N 15/00* (2006.01)
*C12Q 1/68* (2006.01)
*C07H 21/04* (2006.01)
*C07H 21/02* (2006.01)
*C12Q 1/00* (2006.01)
*C12Q 1/34* (2006.01)
*C12Q 1/26* (2006.01)
*C12N 9/00* (2006.01)

(52) U.S. Cl. .......................... 435/254.21; 435/4; 435/6; 435/440; 435/252.3; 435/254.1; 435/183; 435/190; 435/18; 435/25; 435/320.1; 536/23.1; 536/23.2

(58) Field of Classification Search .................. 435/190, 435/183, 4, 6, 18, 25, 252.3, 320.1, 254.1, 435/254.21, 440; 530/350; 536/23.2, 23.1
See application file for complete search history.

(56) References Cited

U.S. PATENT DOCUMENTS

| 5,137,822 | A | 8/1992 | Yabusaki et al. |
| 5,157,135 | A | 10/1992 | Tsuji et al. |
| 5,547,868 | A | 8/1996 | Miller et al. |
| 5,759,801 | A | 6/1998 | Chenivesse et al. |
| 5,989,881 | A | 11/1999 | Chenivesse et al. |
| 5,965,417 | A | 12/1999 | Chenivesse et al. |
| 6,218,139 | B1 | 4/2001 | Achstetter et al. |
| 6,503,749 | B2 | 1/2003 | Achstetter et al. |
| 7,033,779 | B1 | 4/2006 | Cauet et al. |
| 2004/0082025 | A1 | 4/2004 | Dumas et al. |

FOREIGN PATENT DOCUMENTS

| EP | 0340878 | 11/1989 |
| EP | 0 360 361 | 3/1990 |
| EP | 0521780 | 1/1993 |
| EP | 0574941 A2 | 12/1993 |
| EP | 0 727 489 | 8/1996 |
| JP | 19880181571 | 2/1990 |
| JP | 1980071250 | 10/1990 |
| JP | 8242851 | 9/1996 |
| WO | WO 99/16886 | 4/1999 |
| WO | WO 99/25865 | 5/1999 |
| WO | WO 99/40203 | 8/1999 |
| WO | WO 01/25469 | 4/2001 |
| WO | WO 02061109 | 8/2002 |

OTHER PUBLICATIONS

Magdolen et al. Transcriptional control by galactose of a yeast gene encoding a protein homologous to mammalian aldo/keto reductases. Gene. May 31, 1990;90(1):105-14.*
Alani et al. A method for gene disruption that allows repeated use of URA3 selection in the construction of multiply disrupted yeast strains.Genetics. Aug. 1987;116(4):541-5.*
Misoga et al. YPR1 Yeast. Accession No. Q12458 and Accesion No. U28373. EMBL Databases. 1997.*
Winzeler et al. Functional characterization of the S. cerevisiae genome by gene deletion and parallel analysis. Science. Aug. 6, 1999;285(5429):901-6.*
Bruno Dumas et al., "Expression of a bovine P450c17 cDNA in the yeast *Saccharomyeces cerevisiae*," Cytochrome P450, Int'l Conference, Ed. M.C. Lachner John Libbey Eurotext, Paris, 427-530, 1994.
Joakim Norbeck et al., "Metabolic and Regulatory Changes Associated with Growth of *Saccharomyces cerevisiae* in 1.4 M NaCl," J. Biol. Chem., 272, 5544-5554, 1997.
Gilles Cauet et al., "Pregnenolone esterification.in *Saccharomyces cerevisiae*. A potential detoxification mechanism," Eur. J. Biochem. 261, 317-324, 1999.
Catherine DuPort et al., "Self-sufficient biosynthesis of pregnenolone and progesterone in engineered yeast," Nature Biotechnology, 16, 186-189, 1998.
Toshiyuki Sakaki et al., "Expression of Bovine Cytochrome P450c17 cDNA in *Saccharomyces cerevisiae*," DNA, 8, 409-418, 1989.

(Continued)

*Primary Examiner*—Yong D Pak
(74) *Attorney, Agent, or Firm*—J. Darrell Fontenot

(57) ABSTRACT

The present invention relates to novel yeast strains, methods and genetic constructs for their preparation, and their use for the synthesis or modification of steroidal compounds. More particularly, the invention describes strains having a reduced 20αHSD type activity, in particular by modifying the GCY1 and/or YPR1 genes. The yeast strains of the invention make it possible to improve the efficiency of the synthesis or to increase the selectivity or the yields of the method, as well as the quality of the final product. The strains, methods and compounds of the invention are useful in the search for, the development and the production of products with therapeutic or prophylactic activity, in humans or animals, in particular of steroidal derivatives.

6 Claims, 6 Drawing Sheets

OTHER PUBLICATIONS

Figure 1:
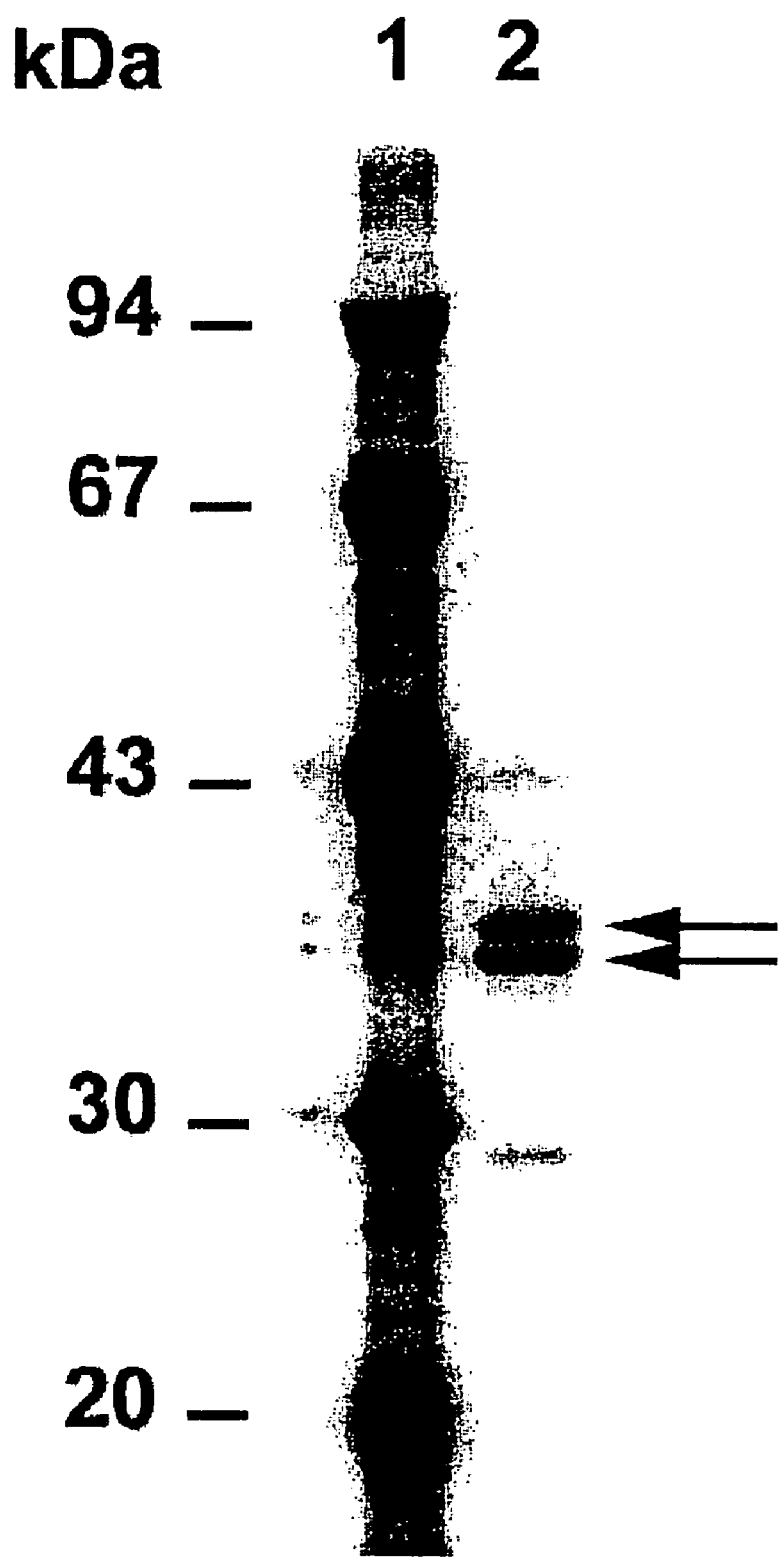

Toshiyuki Sakaki et al., "Progesterone metabolism in recombinant yeast simultaneously expressing bovine cytochromes P450c17 (CYP17A1) and P450c21 (CYP21B1) and yeast NADPH-P450 oxidoreductase," Pharmacogenetics, 1, 86-93, 1991.

Toshiyuki Sakaki et al., "Expression of Bovine Cytochrome P450c21 and Its Fused Enzymes with Yeast NADPH-Cytochrome P450 Reductase in *Saccharomyces cerevisiae*," DNA Cell Bio., 9, 603-614, 1990.

Ulrich Oechsner et al., "A nuclear yeast gene (GCY) encodes a polypeptide with high homology to a vertebrate eye lens protein," FEBS Lett., 238, 123-128, 1988.

Viktor Magdolen et al., "Transcriptional control by galactose of a yeast gene encoding a protein homologous to mammalian aldo/keto reductases," Gene, 90, 105-114, 1990.

Du-An Wu et al., "Expression and Functional Study of Wild-Type and Mutant Human Cytochrome P450c21 in *Saccharomyces cerevisiae*," DNA Cell Bio., 10, 201-209, 1991.

T. Miosga et al., GenBank sequence entry, Accession No. X80642, "S. cerevisiae YPR1 gene for putative reductase 1". Submitted Jul. 26, 1994, revised Feb. 9, 1995.

Altschul et al., Basic Local Alignment Search Tool, J. Mol. Biol. vol. 215, 1990, pp. 403-410.

Ashman et al., Cloning and Disruption of the Yeast C-8 Sterol Isomerase Gene, Lipids, vol. 26, No. 8, 1991, pp. 628-632.

Bach et al., Evidence for transcriptional regulation of orotidine-5'-phosphate decarboxylase in yeast by hybridization of mRNA to the yeast structural gene cloned in *Escherichia coli*, PNAS, vol. 76, No. 1, Jan. 1979, pp. 386-390.

Bard et al., Steroi Mutants of *Saccharomyces cerevisiae*: Chromatographic Analyses, Lipids, vol. 12(8), 1977, pp. 645-654.

Baudin et al., A simple and efficient method for direct gene deletion in *Saccharomyces cerevisiae*, Nucleic Acids Research, vol. 1993, vol. 21, No. 14, pp. 3329-3330.

Clejan et al., Rate of Amphotericin B and Filipin Association with Sterols, J. of Bio. Chem., vol. 260, No. 5, Mar. 10, 1985, pp. 2884-2889.

Corey et al., isolation of an Arabidopsis thaliana gene encoding cycloartenol synthase by functional expression in a yeast mutant lacking lanosterol synthase by the use of a chromatographic screen, PNAS, vol. 90, Dec. 1993, pp. 11628-11632.

Delourme et al., Cloning of an Arabidopsis thaiiana cDNA coding for farnesyl diphosphate synthase by functional complementation in yeast (Abstract only), Plant Mol Biol. vol. 26. No. 6, Dec. 1994, pp. 1867-1873.

Fitzky et al., Mutations in the 7-sterol reductase gene in patients with the Smith-Lemii-Opitz syndrome, PNAS, vol. 95, Jul. 1998, pp. 8181-8186.

Fuji et al., Acetate Ester Production by *Sacharomyces cerevisiae* Lacking the ATF1 Gene Encoding the Alcohol Acetyltransferase, J. of Ferm. and Bioengineering, vol. 81, No. 6, 1996, pp. 538-542.

Gobeil et al., Intracellular Sequestration of Hetero-oligomers Formed by Wild-Type and Glaucoma-Causing Myocilin Mutants, IOVS, vol. 45, No. 10, Oct. 2004, pp. 3560-3567.

Johanson et al., Strain engineering for stereoselective bioreduction of dicarbonyl compounds by yeast reductases, FEMS Yeast Research, vol. 5, 2005, pp. 513-525.

Johnson, Metabolic Interference and the + – Heterozygote. A Hypothetical Form of Simple Inheritance Which Is Neither Dominant nor Recessive. Am. J. Hum Genet, vol. 32, 1980, pp. 374-386.

Kawata et al., Microsomal Enzymes of Cholesterol Biosynthesis from Lanosterol, J. of Biol. Chem., vol. 260, No. 11, Jun. 10, 1985, pp. 6609-6617.

Kissel, Molecular cloning and expression of cDNA for rat pancreatic cholesterol esterase, Biochimica et Biophysica Acta 1006. 1989, pp. 227-236.

Kuromori et al., Cloning of cDNAs from *Arabidopsis thaliana* that encode putative protein phosphatase 2C and a human Dr1-like protein by transformation of a fission yeast mutant, Nucleic Acids Research, vol. 22, No. 24, 1994, pp. 5296-5301.

Lorenz et al., Cloning, Sequencing, and Disruption of the Gene Encoding Sterol C-14 Reductase in *Sacharomyces ceravisiae*, DNA an Cell Biology, vol. 11, No. 9, 1992, pp. 685-692.

Marcireau et al., In Vivo Effects of Fenpropimorph on the Yeast *Saccharomyces cerevisiae* and Determination of the Molecular Basis of the Antifungal Property, Antimicrobial Agents and Chemotheray, vol. 34, No. 6, Jun. 1990, pp. 989-993.

Minet et al., Completion of *Saccharomyces cerevisiae* auxotrophic mutants by *Arabidopsis thaliana* cDNAs, The Plant Journal, vol. 2, No. 3, 1992, pp. 417-422.

Moebius et al., Molecular cloning and expression of the human 7-sterol reductase, PNAS, vol. 95, Feb. 1998, pp. 1899-1902.

Nacken Valerie et al., Probing The Limits Of Expression Levels By Varying Promoter Strength And Plasmid Copy Number in *Saccharomyces cerevisiae*, Gene, (1996), vol. 175, pp. 253-260.

Nagasawa et al., Cloning and Nucleotide Sequence of the Alcohol Acetyltransferase II Gene (ATF2) from *Saccharomyces cerevisiae* Kyokai No. 7., Biosci. Biotechnol. Biochem. vol. 62, No. 10, 1998, pp. 1852-1857.

Newman et al., Genes Galore: A Summary of Methods for Accessing Results from Large-Scale Partial Sequencing of Anonymous Arabidopsis cDNA Clones, Plant Physiol. vol. 106, 1994, pp. 1241-1255.

Oechsner et al., A nuclear yeast gene (GCY) encodes a polypeptide with high homology to a vertebrate eye lens protein, FEB vol. 238, No. 1, Sep. 1988, pp. 123-128.

Opitz et al., Cholesterol Metabolism in the RSH/Smith-Lemil-Optiz Syndrome: Summary of an NICHD Conference, Am. J. of Medical Genetics. vol. 50, 1994, pp. 326-338.

Riou, Isolation and characterization of a cDNA encoding Arabidopsis thaliana mevalonate kinase by genetic complementation in yeast, Gene, vol. 148. 1994, pp. 293-297.

Servouse et al., Isolation and Characterization of Yeast Mutants Blocked in Mevalonic Acid Formation, Biochem & Biophys. Res. Comm., vol. 123, No. 2, Sep. 17, 1984.

Servouse et al., Regulation of early enzymes of ergosterol biosynthesis in *Saccharomyces cerevisiae*, Biochem. J. vol. 240, 1986, pp. 541-547.

Taketani et al., Characterization of Sterol-Ester Synthetase in *Saccharomyces cerevisiae*, Biochimica et Biophysica Acta, vol. 575, 1979, pp. 148-155.

Urban et al., Cloning, Yeast Expression, and Characterization of the Coupling of Two Distantly Related *Arabidopsis thaliana* NADPH-Cytochrome P450 Reductases with P450 CYP73A5, J. of Biol. Chem., vol. 272, No. 31, Aug. 1, 1997, pp. 19176-19186.

Wada et al., Expression of Functional Bovine Cholesterol Side Chain Cleavage Cytochrome P450 (P450scc) in *Escherichia coli*, Arch. of Biochem & Biophysics, vol. 290, No. 2, Nov. 1, 1991, pp. 376-380.

Winston et al., Construction of a Set of Convenient *Saccharomyces csevisiae* Strains that are Isogenic to S288C, Yeast, vol. 11, 1995, pp. 53-55.

Xu et al., Reproducing Abnormal Cholesterol Biosynthesis as Seen in the Smith-Lemil-Optiz Syndrome by Inhibiting the Conversion of 7-Dehydrocholesterol to Cholesterol in Rats, J. of Clinical Investigation, vol. 95, Jan. 1995, pp. 76-81.

Zweytick et al., Contribution of Are1p and Are2p to steryl ester synthesis in the yeast *Saccharomyces cerevisiae*, European Journal of Biochemistry, vol. 267, Issue 4, 2000. pp. 1075-1082.

Ritter et al, Purification and Characterization of a Naturally Occurring Activator of Cholesterol Biosynthesis From 5,7-Cholestadienol and Other Precursors, Biochem & Biophys Res. Comm, vol. 38, No. 5, 1970, pp. 921-929.

Taton et al., Identification of 5,7-Sterol-7- Reductase In Higher Plant Microsomes, Biochem & Biophysical Res. Comm., vol. 181, No. 1, 1991, pp. 465-473.

Dempsey, M.E., Sterol 50Dehydrogenase and 7-Reductase, Methods in Enzymology, vol. 15, 1969 pp. 501-504.

Accession No. XP-002084827, 1996.
Accession No. XP-002084826, 1997.
Accession No. XP-002165509, 1990.
Accession No. XP-002165510, 1990.

Anderson et al. Cloning, Structure and Expresion of the Mitochondrial Cytochrome, P-450 Sterol 26-Hydroxylase, a Bile Acid Biosynthetic Enzyme, J. of Biol. Chem., vol. 264, No. 14, May 15, 1989, pp. 8222-8229.

Saunders-Singer, Ascus Dissection, Methods in Molecular Biology, Vo.. 53, Yeast Protocols, pp. 59-67, 2009.

Wach, at al., 5-PCR Based Gene Targeting in *Saccharomyces cerevisiae*, Methods in Microbiology, vol. 26, 1998, Chapter 5.

Branden et al, Introduction to Protein Structure, Garland Publishing Inc., New York, 1991, p. 247.

Seffernick et al., Melamine Deaminase and Atrazine Chlorohydrolase: 98 Percent Identical but Functionally Different, J. Bacteriology, vol. 183, No. 8, pp. 2405-2410, 2001.

Witkowski et al., Conversion of a Beta-Ketoacyl Synthase to a Malonyl Decarboxylase by Replacement of the Active-Site Cysteine with Glutamine, Biochemistry, vol. 38, 1999, pp. 11643-11650.

Sousa et al., The ARO4 gene of Candida albicans encodes a tyrosine-sensitive DAHP synthase: evolution, functional conservation and phenotype of Aro3p-Aro4p-deficient mutants, Microbiology, vol. 148, 2002, pp. 1291-1303.

Arreguin De Lorencez et al., Regulation of Gluconeogenic Enzymes During the Cell Cycle of *Saccharomyces cerevisiae* Growing in a Chemostat, J. of General Microbiology, vol. 133, 1987, pp. 2517-2522.

Bonneaud et al., A Family of Low and High Copy Replicative, Integrative and Single-Stranded *S. cerevisiae/E. Coli* Shuttle Vectors, Yeast, vol. 7, 1991, pp. 609-615.

Burgers Peter M. J. et al., Transformation Of Yeast Spheroplasts Without Cell Fusion. Analytical Biochemistry, (1987), vol. 163, pp. 391-397.

Cauet Gilles et al., CYP11A1 Stimulates The Hydroxylase Activity Of CYP11B1 in Mitochondria of Recombinant Yeast In Vivo and In Vitro, European Journal of Biochemistry (2001) 268 pp. 4054-4062.

Chua Streamson C. et al., Cloning of cDNA Encoding Steroid 11 Beta-Hydroxylase (P450c11), Proc. Natl. Acad. Sci. USA, (1987), vol. 84, pp. 7193-7197.

Degryse E et al., Pregnenolone Metabolized to 17 Gamma Hydroxyprogesterone in Yeast: Biochemical Analysis of A Metabolic Pathway, Journal of Steroid Biochemistry & Molecular Biology (1999) pp. 239-246.

Degryse Eric et al., In Vivo Cloning by Homologous Recombination in Yeast Using A Two-Plasmid-Based System. Yeast, (1995), vol. 11. pp. 629-640.

Degryse Eric In Vivo intermolecular Recombination in *Escherichia Coli*: Application to Plasmid Constructions, Gene, (1996), vol. 170, pp. 45-50.

Dumas Bruno et al., 11 Beta-Hydroxylase Activity In Recombinant Yeast Mitochondria in Vivo Conversion Of 11-Deoxycortisol To Hydrocortisone, European Journal of Biochemistry (1996) 238 pp. 495-504.

Hu Meng-Chun et al., Expression of Human 21-Hydroxylase (P450c21) in Bacterial and Mammalian Cells A System to Characterize Normal and Mutant Enzymes, Molecular Endocrinology, (1990), vol. 4, pp. 893-898.

Kawamoto Takeshi et al., Cloning Of cDNA and Genomic DNA for Human Cytochrome P-45011 Beta, FEBS, (1990), vol. 269, No. 2. pp. 345-349.

Kuronen Pirjo et al., Reversed—Phase Liquid Chromatographic Separation and Simultaneous Profiling of Steroidal Glycoalkaloids and Their Aglycones, Journal of Chromatography A, (1999), vol. 863, pp. 25-35.

Lacour Thierry et al., Characterization Of Recombinant Adrendoxin Reductase Homologue (Arhip) From Yeast, The Journal Of Biological Chemistry (1998) 273 pp. 23984-23992.

Lathe R. et al., Plasmid and Bacteriophage Vectors for Excision Of Intact Inserts, Gene, (1987), vol. 57, pp. 193-201.

Lecain Eric et al., Cloning by Metabolic Interference in Yeast and Enzymatic Characterization Of Arabidopsis Thaliana Sterol Delta 7-Reductase, The Journal Of Biological Chemistry. (1996), vol. 271, No. 18, pp. 10866-10873.

Li Jie et al., Adrenodoxin Reductase Homolog (Arhlp) of Yeast Mitochondria Required for Iron Homeostasis, the Journal Of Biological Chemistry (2001) pp. 1503-1509.

Parent Stephen A. et al., Vector Systems for the Expression, Analysis and Cloning of DNA Sequences in *S. cerevisiae*, Yeast. (1985), vol. 1, pp. 83-138.

Riesenberg D. et al., High-Cell-Density Cultivation of Microorganisms, Appl Microbiol Biotechnology, (1999), vol. 51, pp. 422-430.

Skaggs B.A. et al., Cloning and Characterization of the *Saccharomyces Cervisiae* C-22 Sterol Desaturase Gene, Encoding a Second Cytochrome P-450 Involved in Ergosterol Biosynthesis, Gene (1996) pp. 105-109.

Szczebara Florence Menard et al., Total Biosynthesis Of Hydrocortisone From a Simple Carbon Source in Yeast, Nature Biotechnology (2003) 21 pp. 143-149.

Thierry Agnes et al., The Complete Sequence of the 8.2kb Segment Left Of MAT On Chromosome III Reveals Five ORFs, Including a Gene for a Yeast Ribokinase, Yeast, (1990), vol. 6, pp. 521-534.

Urban Philippe et al., Characterization Of Recombinant Plant Cinnamate 4-Hydroxlase Produced in Yeast Kinetic and Spectral Properties Of the Major Plant P450 Of the Phenylpropanoid Pathway, European Journal Of Biochemistry, (1994), vol. 222, pp. 843-850.

Valvo L. et al., General High-Performance Liquid Chromatographic Procedures for the Rapid Screening Of Natural and Synthetic Corticosteroids, Journal Of Pharmaceutical & Biomedical Analysis, (1994). vol. 12, No. 6, pp. 805-810.

Wu et al., Expression and Functional Study of Wild-Type and Mutant Human Cytochrome P450c21 in *Saccharomyces cerevisiae*, DNA and Cell Biology, vol. 10, No. 3, 1991,pp. 201-209.

Yang Hongyuan et al., Sterol Esterificatio in Yeast: A Two-Gene Process, Science (1996) 272 pp. 1353-1356.

Yanisch-Perron Celeste et al., Improved M13 Phage Cloning Vectors and Host Strains: Nucleotide Sequences Of the M13mpl8 and pUC19 Vectors, Gene, (1985), vol. 33. No. 1, pp. 103-119.

Zhao Hui-Fen et al., Molecular Cloning, cDNA Structure and Predicted Amino Acid Sequence Of Bovins 3Beta-Hydroxy-5-Ene Steroid Dehydrogenase/Gamma5-Gamma4 isomerase, FEB, (1989), vol. 259, No. 1, pp. 153-157.

PSI-BLAST Results GCY1/YOR120W, http://db.yeastgenome.org/cgi-bin/homolog/uniprotHomolog?locus=YOR120W, accessed Nov. 29, 2006.

PSI-BLAST Results, YPR1/YDR388W, http://db.yeastgenoe.org/cgi-bin/homolog/uniprotHomolog?locus=YDR368W, accessed Nov. 29, 2006.

\* cited by examiner

US 7,879,592 B2

MODIFIED YEASTS AND USES THEREOF, IN PARTICULAR FOR PRODUCING STEROID DERIVATIVES

The present invention relates to the biological and pharmaceutical fields. It relates in particular to novel compositions and methods useful for the production of steroidal compounds, or for the (selective) conversion of steroidal compounds. It relates more particularly to novel yeast strains and genetic methods and constructs for their preparation, and to their use for the synthesis or modification of steroidal compounds. The yeast strains of the invention make it possible to improve the efficacy of synthesis and to increase the selectivity or the yields of the method, and the quality of the final product. The strains, methods and compounds of the invention are useful in research, development and production of products with therapeutic or prophylactic activity, in humans or animals, in particular of steroidal derivatives.

The natural capacity of microorganisms to convert steroids has been widely described in the literature. In this regard, they represent an advantageous alternative for the production of steroidal derivatives which are difficult to obtain by chemical synthesis. Yeasts are moreover particularly suitable for the expression of cDNA encoding enzymes which are active in organelles. As a result, yeasts, such as *S. cerevisiae*, have been widely used to express cDNAs encoding steroidogenic enzymes such as microsomal or mitochondrial P450s. Furthermore, some studies intended to express enzymes involved in the pathway for the biosynthesis of hydrocortisone have made it possible to show that yeasts were capable of efficiently converting certain intermediates. Thus, the use of transformed yeasts allowing the expression of one or more mammalian enzymes involved in the pathway for the biosynthesis of steroids has been described for example in application EP340878, patent U.S. Pat. No. 5,137,822 or in Dumas et al. Likewise, the applicants have found that $\Delta^5$-3β-hydroxysteroids such as pregnenolone, 17α-hydroxypregnenolone and DHEA were converted by yeasts to the corresponding acetate esters. The applicants have also demonstrated that this conversion was essentially performed by the product of the ATF2 gene (Cauet et al., 1999). Yeasts therefore represent a particularly useful organism from the industrial point of view for the production of steroidal derivatives.

However, it is also known that 17α-hydroxyprogesterone may, under certain conditions, be reduced by yeasts to 4-pregnene-17α,20α-diol-3-one (Dumas et al., 1994) and that the production of this by-product affects the yields of synthesis and the quality of the final product. However, up until now, the enzymatic activity or activities responsible for this reaction, of the 20α-hydroxysteroid dehydrogenase (20αHSD) type, has/have not been identified.

The present invention results precisely from the study of the endogenous activities of yeast acting on hydroxyprogesterone and describes the identification of two genes encoding enzymes endowed with 20αHSD type activity. More particularly, the present application shows that the GCY1 and YPR1 genes are carriers of the 20αHSD type activity in yeast, and that the product of these genes makes it possible, for example, to convert hydroxyprogesterone to by-products in vitro. The present application shows, moreover, that the suppression of the activity of these genes in yeast considerably reduces or suppresses the formation of by-products of 4-pregnene-17α, 20α-diol-3-one type, and makes it possible to significantly improve the yields of synthesis of steroidal derivatives and/or to convert hydroxyprogesterone (or its precursors) to steroidal derivatives in a more selective manner. The present application therefore describes novel compositions and methods which can be used for the synthesis of steroidal derivatives with better selectivity. The invention describes, in particular, novel yeast strains having a reduced 20αHSD type activity and essentially incapable of converting hydroxyprogesterone to 4-pregnene-17α,20α-diol-3-one type by-products. The invention may also be used to increase the production of such products, for their use or conversion to active compounds.

A first subject of the invention consists more particularly in a method for modifying a steroid compound, comprising bringing this compound (or a precursor thereof) into contact with a yeast having a reduced 20αHSD activity, in particular a yeast having a nonfunctional, in particular disrupted, GCY1 and/or YPR1 gene, more preferably a yeast of the genus Saccharomyces, or a preparation derived from such a yeast.

The invention also relates to the use of a yeast having a reduced 20αHSD activity, in particular a yeast having a nonfunctional, in particular disrupted, GCY1 and/or YPR1 gene, more preferably a yeast of the genus Saccharomyces, or a preparation derived from such a yeast, for the preparation, production, synthesis, modification and/or improvement of steroidal compounds in vitro or ex vivo.

The invention also relates to any method for producing steroidal derivatives from hydroxysteroid compounds, in particular hydroxyprogesterone or its precursors, using a yeast having a reduced 20αHSD type activity, in particular a yeast having a nonfunctional, in particular disrupted, GCY1 and/or YPR1 gene, more preferably a yeast of the genus Saccharomyces, or a preparation derived from such a yeast.

The invention also relates to a method for converting 17α-hydroxyprogesterone, in particular to 11-deoxycortisol, using a yeast having a reduced 20αHSD type activity, in particular a yeast having a nonfunctional, in particular disrupted, GCY1 and/or YPR1 gene, more preferably a yeast of the genus Saccharomyces, or a preparation derived from such a yeast.

The subject of the invention is also the use of a yeast having a reduced 20αHSD activity, in particular a yeast having a nonfunctional, in particular disrupted, GCY1 and/or YPR1 gene, more preferably a yeast of the genus Saccharomyces, or a preparation derived from such a yeast, for the conversion of 17α-hydroxyprogesterone to 11-deoxycortisol.

Another subject of the invention further consists in a method for modifying the 20αHSD type activity of a yeast, comprising the modification of the activity of the GCY1 and/or YPR1 gene of the said yeast. It involves more particularly a method for reducing or inhibiting the 20αHSD activity of a yeast, comprising the inactivation of the GCY1 and/or YPR1 gene of the said yeast, preferably by gene disruption, more preferably still on yeasts of the genus Saccharomyces.

The subject of the present invention is also particular strains of yeast having a reduced 20αHSD type activity. More preferably, this involves yeasts possessing a nonfunctional YPR1 gene, yeasts possessing a nonfunctional GCY1 gene and YPR1 gene, or certain yeasts possessing a nonfunctional GCY1 gene.

The invention also relates to any acellular preparation derived from a yeast as described above, in particular a cellular lysate, a cellular homogenate, a culture supernatant, or a derived enriched or (pre-purified) solution, and the like.

As indicated above, the present invention describes, for the first time, yeast strains (or cells or cultures), and derived preparations, having a reduced, or undetectable, 20αHSD type activity. The invention indeed describes the identification of yeast genes carrying this activity, the GCY1 and YPR1 genes, and shows that these genes can be specifically modified, in particular by means of genetic recombination techniques, without harming the growth or survival capacity of the cells, or their ability to transform or convert steroidal compounds. The invention thus provides, for the first time, methods for the synthesis, production, modification and/or conversion of steroidal compounds using advantageous yeasts.

A subject of the invention therefore consists, more particularly, in the use of a yeast strain (or cell or culture), characterized in that it possesses a genetic modification and in that it has a reduced 20αHSD activity, for the production of steroidal compounds. The present invention uses, more particularly, a yeast strain, characterized in that it possesses:
- a genetic modification of the GCY1 gene, or
- a genetic modification of the YPR1 gene, or
- a genetic modification of the GCY1 and YPR1 genes.

More preferably, the genetic modification(s) present in the yeasts of the invention are inactivating modifications, that is to say which lead to the loss of activity of the gene and/or of the corresponding protein. A most particularly preferred type of inactivating genetic modification according to the invention is a gene disruption, as will be described in detail in the remainder of the text.

More specifically, the invention therefore consists in the use of yeasts in which:
- the GCY1 gene is nonfunctional,
- the YPR1 gene is nonfunctional, or
- the GCY1 and YPR1 genes are nonfunctional, for the preparation of steroidal compounds.

Such yeasts possess a reduced, or undetectable, 20αHSD activity, and are therefore particularly advantageous for the production or the modification or the conversion of steroidal compounds.

According to a preferred embodiment of the invention, the yeasts belong more preferably to the genus Saccharomyces, in particular S. cerevisiae. Thus, in a more specific embodiment, the present invention consists in methods or uses of cells (or strains or cultures) of yeast of genus S. cerevisiae comprising a nonfunctional, preferably disrupted, GCY1 gene and/or YPR1 gene.

However, although the examples relate more specifically to the yeast Saccharomyces cerevisiae, it is understood that the teaching of the invention is not limited to this particular type of yeasts and may be essentially extended to any yeast having a natural activity of the 20αHSD type or containing a GCY1 or YPR1 gene. In this context, there may be mentioned in particular the yeasts Saccharomyces, Kluyveromyces (in particular K. lactis), Schizosaccharomyces, Hansenula, Pichia (in particular P. pastoris), Candida (in particular C. maltosa), and the like, whose culture in fermenters and genetic modification have been described in the prior art.

Moreover, for the purposes of the invention, the expression GCY1 gene is understood to mean the S. cerevisiae GCY1 gene as described in GenBank under the reference X96740 (Bandlow et al., Gene 90(1), 1990, 105-114), as well as any functional variant or homologue thereof present in yeast cells. Similarly, the YPR1 gene denotes the S. cerevisiae YPR1 (or YDR368w) gene as described in GenBank under the reference X80642, as well as any functional variant or homologue thereof present in yeast cells. The sequence of these genes may also be obtained from other banks in which the complete sequence of the genome of the yeast S. cerevisiae is described (Stanford University, MIPS, and the like). The functional homologues may be identified by a search for sequence homologies, or by hybridization cloning, using probes derived from S. cerevisiae GCY1 and YPR1 genes, according to conventional molecular biology techniques.

As indicated, the present invention consists in methods or uses of yeasts exhibiting a genetic modification of one or more genes involved in the 20αHSD activity, in particular the GCY1 and/or YPR1 genes, and preferably having a reduced, or even suppressed, 20αHSD activity.

For the purposes of the invention, the term "genetic modification" denotes any alteration of the genome of a cell, obtained by any possible method, such as the use of mutagenic agents and/or the production of modification(s) by the genetic or recombinant route. Preferably, a genetic modification is a modification of the sequence of at least one gene, resulting in the modification of the activity of the gene, and in particular in the stimulation or, preferably, the inactivation of the said gene. The inactivation of a gene, or the nonfunctional character of a gene, can manifest itself by the absence of expression of a protein, by the expression of a nonfunctional form of the protein, because of mutation(s), deletion(s), substitution(s), insertion(s), and the like, or by the expression of the protein in low levels, not allowing sufficient activity. As a result, the genetic modification of a gene may affect in particular all or part of the coding region of the said gene or of a regulatory region of the said gene (promoter and the like).

Preferably, the genetic modification according to the invention comprises at least one mutation, substitution, deletion and/or insertion of one or more base pairs in the regulatory or coding region of the gene considered. More preferably still, it involves a modification via deletion of all or part of the gene considered, which may be replaced by foreign sequences, according to the gene disruption (or "gene replacement") technique. Genetic modifications via deletion and/or insertion are preferred for carrying out the present invention since they are selective for the gene considered and are stable over time. More preferably, the genetic modification therefore consists in the replacement of at least part of the gene considered with foreign sequences. This modification may be accomplished by known techniques consisting in preparing a modified gene in vitro, which may be introduced into the genome of yeasts by double homologous recombination, as described in the examples (also see Baudin et al., Nucleic Acids Res. 21(14) (1993) 3329).

Thus, a preferred subject of the invention consists in methods or uses of yeasts in which all or part of the GCY1 and/or YPR1 gene has been replaced by foreign (or heterologous) sequences, for example by a marker gene (encoding resistance to an antibiotic). More particularly, for gene disruption, a recombinant nucleic acid is prepared in vitro, comprising a chosen foreign sequence bordered by sequences homologous to contiguous or noncontiguous regions of the gene considered. The foreign sequence may be for example a marker gene, a gene complementing an auxotrophy, an expression unit, and the like. More particularly, the foreign sequence may be an auxotrophic selection gene complementing a nutritional requirement in the host yeast strain, such as the URA3 gene, LEU2 gene, TRP1 gene, HIS3 gene or ADE2 gene for example; a dominant selection gene, such as a gene for resistance to an antibiotic (G418, phleomycin, hygromycin B, and the like); or a reporter gene (β-galactosidase, and the like). It may also be an expression interrupting unit, comprising, for example, a transcriptional terminator such as in particular a yeast terminator chosen from CYC1, TDH3, TEF1 or PGK. It is understood that any other foreign sequence (i.e., not naturally present in this form in the gene considered) making it possible to alter the conditions for expression of the gene and/or the actual structure of the protein encoded may be used in the context of the present invention. The nucleic acid thus prepared is then introduced into the yeasts, by conventional techniques (lithium, protoplasts, and the like), leading to the insertion of the foreign sequence into the genome of the yeast, within the sequence of the gene considered, optionally as a replacement for a region thereof, by double homologous recombination.

It is understood that any other genetic modification technique may be used in the context of the present invention, such as for example site-directed mutagenesis, the use of transposons and the like.

Specific examples of yeasts having a GCY1 and/or YPR1 gene inactivated by gene disruption are in particular:

the TGY170 cells (gcy1::LEU2): in the TGY170 cells, a portion of the GCY1 gene has been replaced by a nucleic acid encoding the LEU2 protein allowing selection of the recombinants.

The TGY197 cells (gcy1::LEU2, ydr368w::URA3): the TGY197 cells comprise, in relation to the TGY170 cells, an additional genetic modification affecting the YPR1 (also designated YDR368w) gene, in which a portion has been replaced by the selection gene URA3.

The TGY195 cells (ydr368w::URA3): the TGY195 cells comprise a genetic modification affecting the YPR1 (also designated YDR368W) gene, in which a portion has been replaced by the selection gene URA3.

The TGY194 cells (gcy1::URA3): in the TGY194 cells, a portion of the GCY1 gene has been replaced by a nucleic acid encoding the URA3 protein allowing selection of the recombinants.

Such cells also constitute a particular subject of the invention. In particular, the invention relates to any yeast cell (or strain or culture) comprising a genetic modification of the (or in the) YPR1 gene, in particular a deletion and/or an insertion of the or in the YPR1 gene. The invention also relates to any yeast cell (or strain or culture) comprising a genetic modification of the (or in the) GCY1 and YPR1 genes, in particular a deletion and/or an insertion of the or in the GCY1 and YPR1 genes. The invention also relates to acellular preparations derived from such yeasts.

The cells of the invention or used in the methods of the invention advantageously have a reduced 20αHSD type activity, that is to say reduced by at least 20%, preferably by at least 40%, more preferably by at least 60%, relative to the nongenetically-modified strain. As is shown in the examples, the invention demonstrates that the inactivation of the GCY1 gene in yeast leads to a 95% reduction in the 20αHSD type activity in the supernatant of a cellular homogenate. The results obtained also show that the double genetic modification of the GCY1 and YPR1 genes leads to the suppression of the 20αHSD type activity, which is then undetectable in the supernatant of a cellular homogenate. These results provide the demonstration of the role of these genes, and illustrate the possibility of modifying them in order to improve the properties of the yeasts, for the applications of production of steroidal derivatives.

The present invention can be used for the production of steroidal compounds, for various pharmaceutical applications. In this regard, the invention describes methods for producing steroidal compounds using the yeasts of the invention. The application also consists in improved methods for producing steroidal compounds using yeasts having a reduced 20αHSD activity. The methods of the invention are advantageously carried out by bringing a population of yeasts as described above into contact, in vitro, with a steroidal compound, followed by extraction of compounds synthesized. The initial steroidal compound may be any natural or modified or synthetic steroid, in particular any hydroxysteroid or precursor compound, in particular cholesterol, progesterone, pregnenolone or 17OH-progesterone. The methods of the invention can be used for the production of steroidal derivatives such as 11-deoxycortisol, cortisol, hydrocortisone, and the like, or derivatives thereof.

Other aspects and advantages of the present invention will emerge on reading the examples which follow, which should be considered as illustrative and nonlimiting.

LEGEND TO THE FIGURES

FIG. 1: SDS-PAGE analysis of a purified fraction of the 20αHSD activity by chromatography on Red120-Agarose from a yeast homogenate. The top arrow indicates the band whose N-terminal sequence corresponds to GCY1, the bottom arrow, that corresponding to the N-terminal sequence of YPR1. Lane 1 corresponds to the molecular weight marker while lane 2 corresponds to the purified fraction of the 20αHSD activity.

Figure 2:
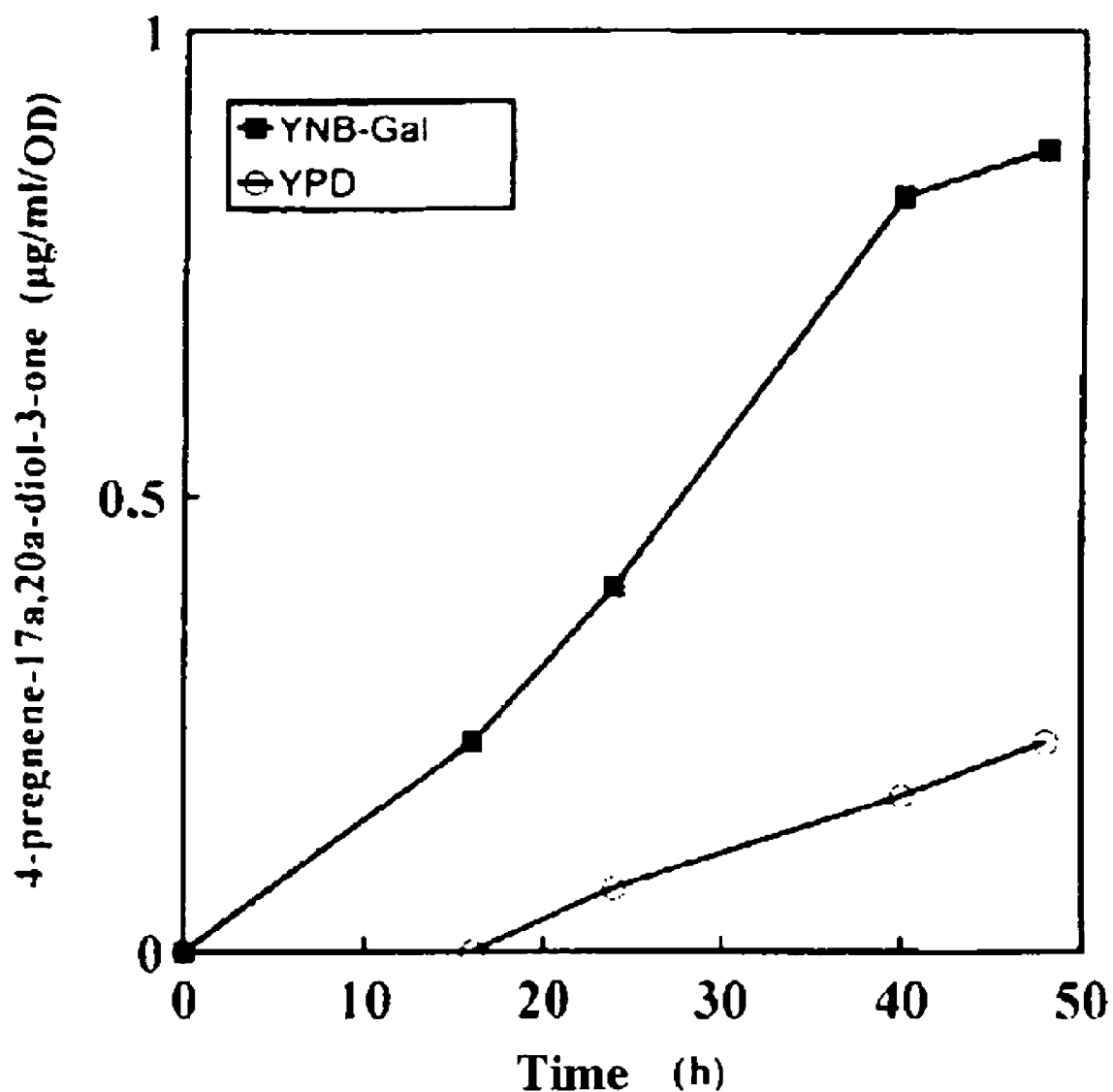

FIG. 2: production of 4-pregnene-17α,20α-diol-3-one by yeasts S. cerevisiae cultured in galactose (YNB-gal) or glucose (YPD) medium in the presence of 0.1 mg/ml of 17α-hydroxyprogesterone.

Figure 3:
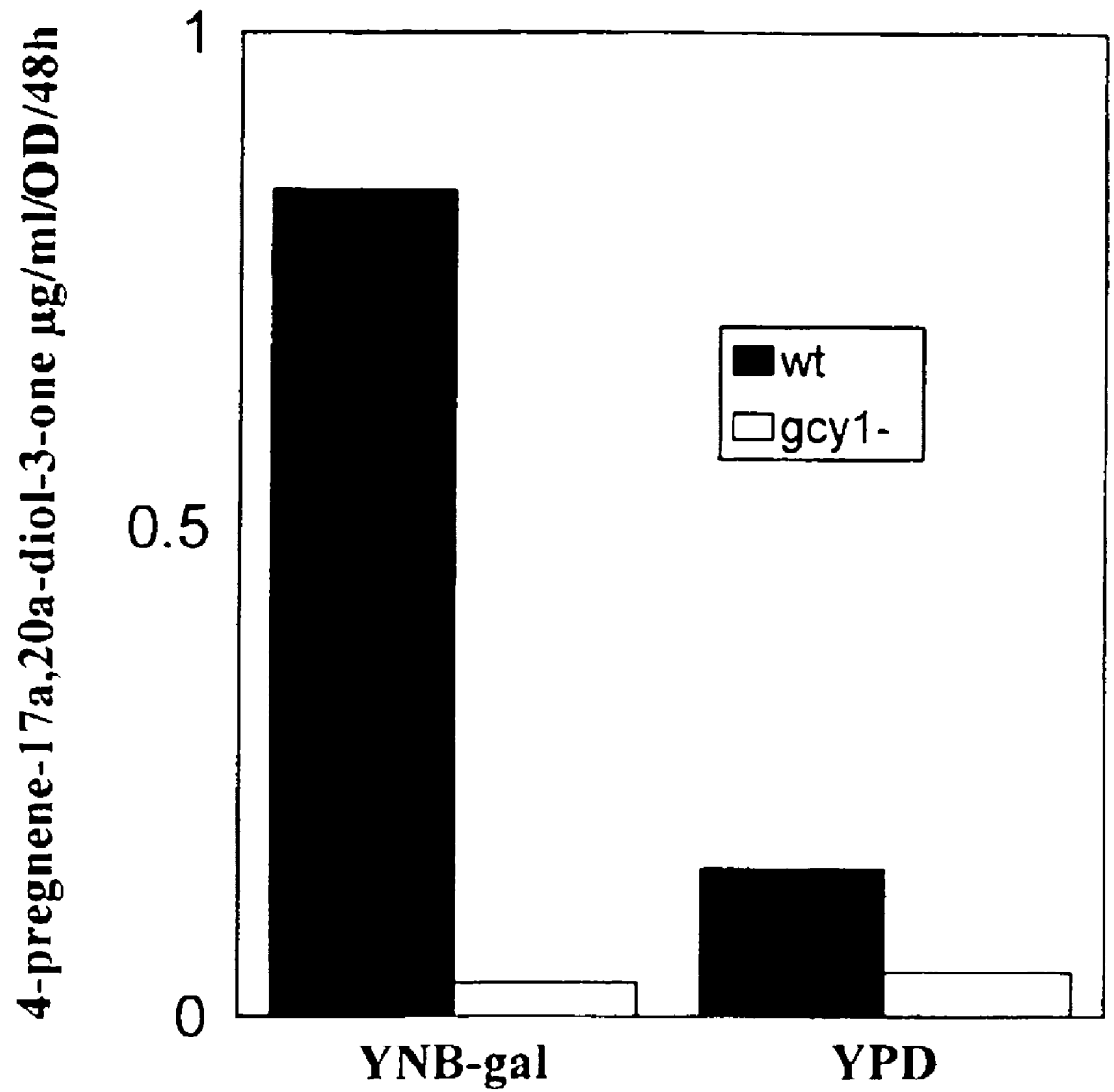

FIG. 3: production of 4-pregnene-17α,20α-diol-3-one by yeasts S. cerevisiae of the wild type (wt) or mutated in the sequence of the GCY1 gene (gcy−) cultured in galactose (YNB-gal) or glucose (YPD) medium in the presence of 0.1 mg/ml of 17α-hydroxyprogesterone.

Figure 4:
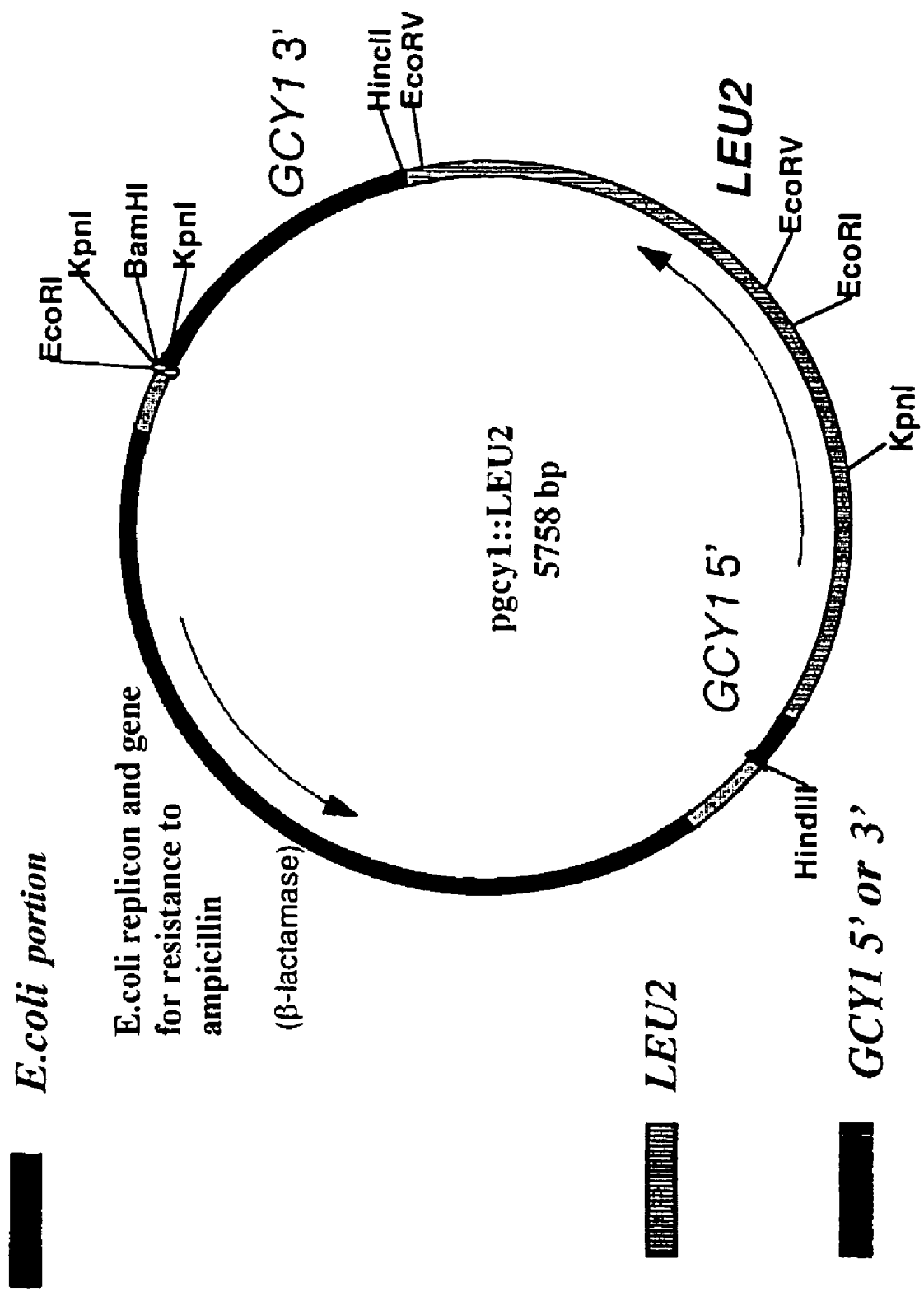

FIG. 4: structure of the plasmid for disrupting the GCY1 gene. The plasmid is linearized with the enzymes BamHI and HindIII and then transformed in S. cerevisiae according to the method described in the section Materials and Methods. The deletion of the sequence of the GCY1 gene comprises the promoter and 306 bp of coding sequence, including the start codon for translation.

Figure 5:
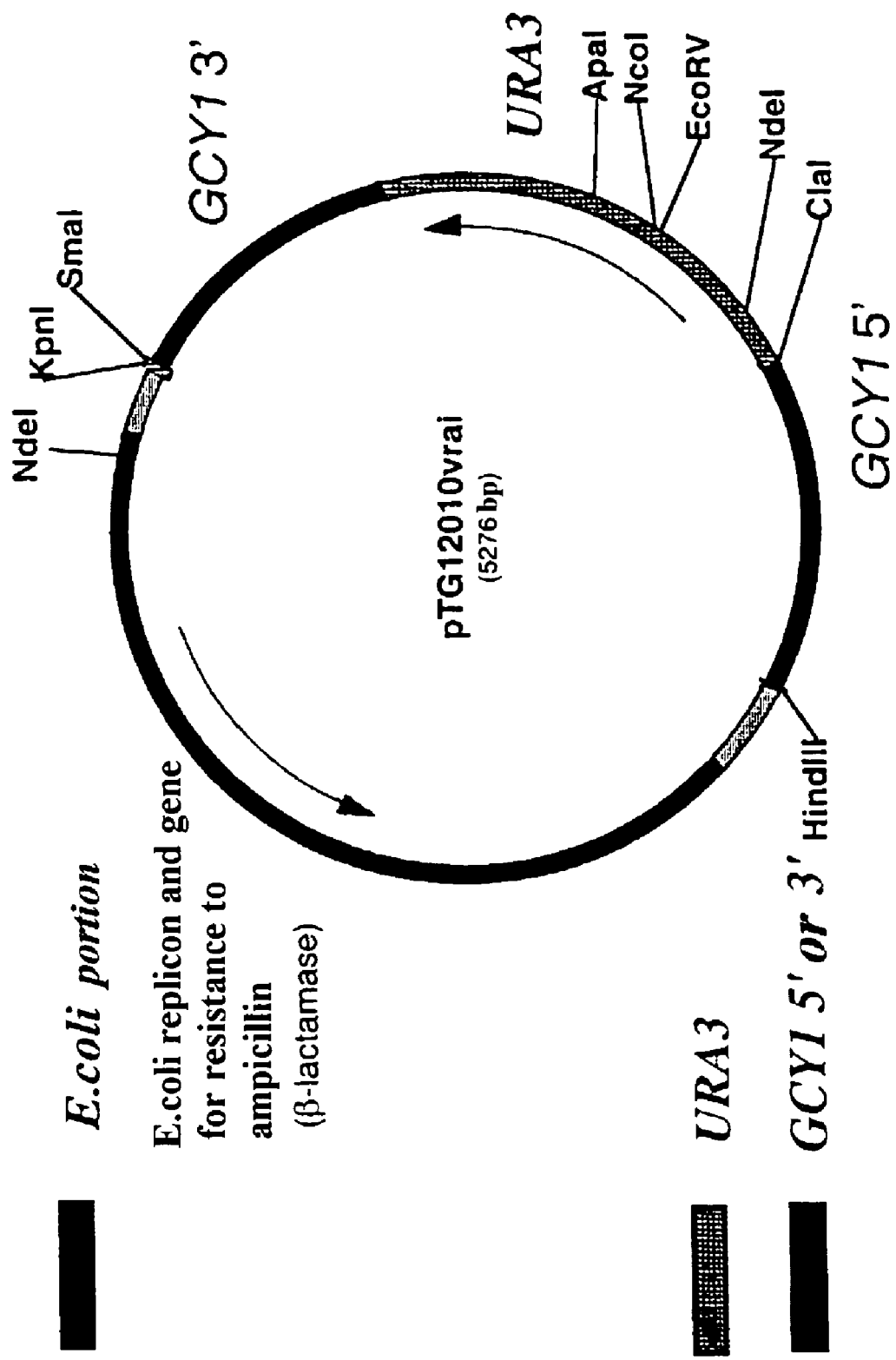

FIG. 5: structure of the plasmid for disrupting the GCY1 gene (plasmid pTG12010 clone 40). The plasmid is linearized with the enzymes EcoRI and SphI and then transformed in S. cerevisiae according to the method described in the section Materials and Methods. The deletion of the protein sequence of GCY1 comprises amino acids 47 to 268 inclusive. pTG12010 clone 36 possesses the same structure, without the ClaI site in 5' of the URA3 gene but with a HindIII site in 3' of the URA3 gene.

Figure 6:
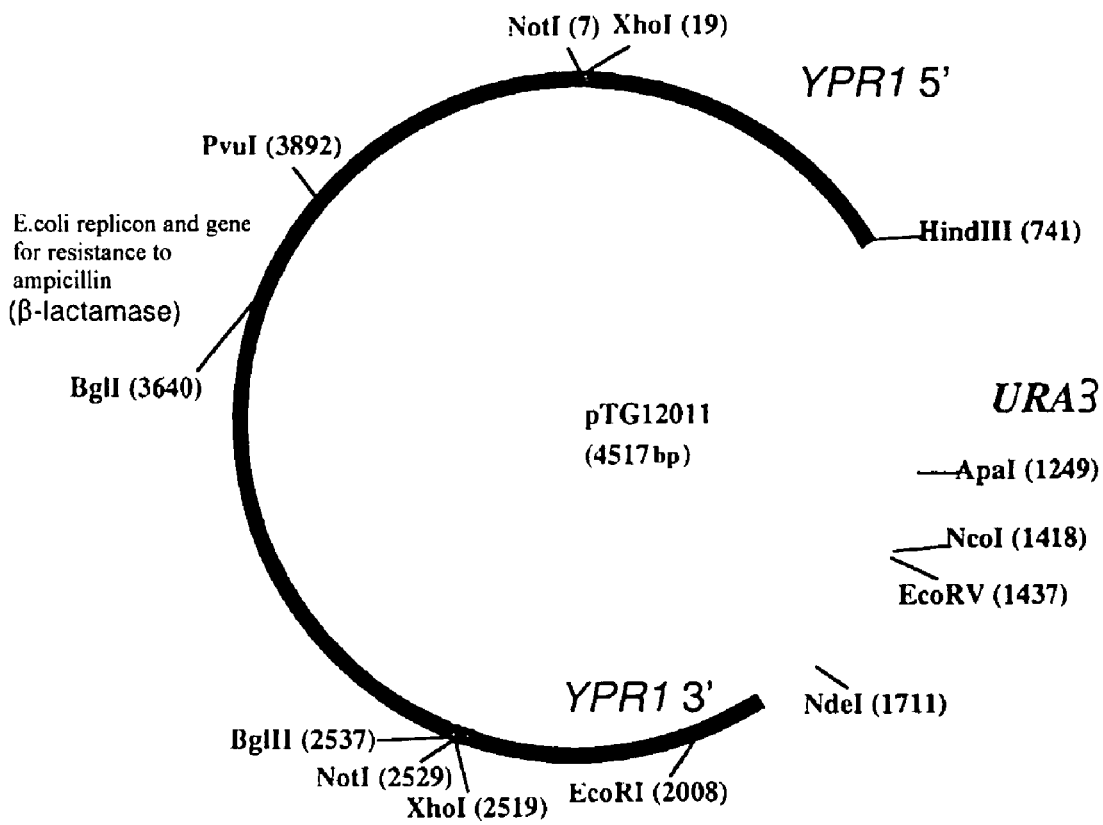

FIG. 6: structure of the plasmid for disrupting the YPR1 gene (YDR368w) (plasmid pTG12011). The plasmid is linearized with the enzyme XhoI and then transformed in S. cerevisiae according to the method described in the section Materials and Methods. The deletion of the protein sequence of YPR1 comprises amino acids 5 to 198 inclusive.

MATERIALS AND METHODS

Chemical products: 17α-hydroxyprogesterone was obtained from Hoechst Marion Roussel (Romainville, France). Tergitol Nonidet P40 and Tyloxapol were obtained from Sigma.

Enzymatic test:

Conversion in vivo of 17α-hydroxyprogesterone: the yeast cells were cultured at 28° C. in YPD medium (10 ml) inoculated at $A_{600}$=0.1 from a 24 h preculture. 100 µl of a 17α-hydroxyprogesterone solution (10 mg/ml) in a Tergitol and ethanol mixture (1/1; v:v) were then added to the culture. Aliquots of culture broth (250 µl) were collected at various intervals and the steroids were extracted with dichloromethane. The steroids were then separated on Ultrasphere ODS in the presence of 45% aqueous acetonitrile at a flow rate of 1 ml/min, at 45° C. These steroids were detected at 240 nm.

Cells:

The *E. coli* BJ5183 strain (Hanahan, 1983) was used for the recombinations in vivo and the strain C600, hsdR (Hubacek and Glover, 1970) for the conventional ligation reactions.

The parental strain of yeast FY1679-28c (MATa ura3-52 trp1-63, leu2-1fen1 his3-200GAL) (Thierry et al., 1995) was used. The strains TGY170, TGY197, TGY195, TGY194, TGY212, TGY245 and FY1679-28c/pTG10497 were constructed as described in the examples.

Conventional methods of molecular biology and of recombination in vivo in *E. coli* and in yeast were used, as described in Sambrook et al. (1989) or in Degryse et al. (1995, 1996).

Culture of the yeasts:

The yeasts were generally cultured on synthetic minimum medium (Sherman, 1991) supplemented with nutritional supplies at 100 µg/ml. For the transformations of *S. cerevisiae*, the cells were made competent according to the lithium acetate technique (Ito et al., 1983), after growth on YPD medium (Sherman, 1991).

Results

Identification of the 20αHSD activity in yeast, responsible for unwanted reactions on 17α-hydroxyprogesterone The NADPH-dependent reduction of 17α-hydroxyprogesterone on C20 to 4-pregnene-17α,20α-diol-3-one by the yeast *S. cerevisiae* has been previously described (Dumas et al., 1994). This activity is similar to the 20αHSD activity reported in various tissues. The enzymes characterized from these tissues are monomeric, with a molecular weight of about 35 kDa. With the aim of identifying the enzyme(s) responsible for the 20αHSD activity in yeast, searches for homologies with the enzyme 20αHSD from bovine testes in *S. cerevisiae* banks were carried out. These searches made it possible to identify 6 products of yeast genes exhibiting 44 to 32% amino acid sequence identity with the mammalian enzyme. These genes are assembled in Table I.

With the aim of better characterizing the enzymes involved, the yeast 20αHSD type activity was reconstituted in vitro using 17α-hydroxyprogesterone and NADPH as substrates. Various preparations derived from *S. cerevisiae* yeast culture were tested in this system, which allowed localization of the activity in the supernatant after centrifugation at 100,000×g of a cellular homogenate. This result indicates that the enzymatic activity is soluble. Partial purification of the 20αHSD type activity by Red 120 chromatography was then carried out, which allowed the production of a doublet in the 35 kDa region, after SDS-PAGE (FIG. 1). The sequencing of these bands showed that they were mainly composed of the product of the GCY1 and YPR1 genes. These two enzymes form part of the bovine homologues of 20αHSD which are listed in Table I. The complete sequence of the GCY1 and YPR1 genes is accessible, for example, in GenBank under the references X96740 and X80642, respectively.

It is advantageous to note that GCY1 has been described as encoding aldo-keto-reductase (AKR) whose expression is significantly increased in the presence of galactose (Magdolen et al., Gene 90(1), 1990, 105). The AKR enzymes have a broad substrate specificity. They metabolize various substrates, including the aliphatic aldehydes, monosaccharides, prostaglandins and steroids. Thus, GCY1 constitutes a good potential candidate, and we decided to verify if this enzyme could be involved in the generation of 4-pregnene-17α,20α-diol-3-one from 17α-hydroxyprogesterone.

Inducible character of the 20αHSD activity and expression in an acellular system The experiments carried out made it possible to demonstrate that the 20αHSD activity is inducible by galactose in yeast. Thus, the conversion in vivo of 17α-hydroxyprogesterone to 4-pregnene-17α, 20α-diol-3-one was determined in yeast cultures cultured on various carbon sources. The delay observed when the yeasts are cultured on glucose was not observed in the presence of galactose (FIG. 2). This observation is in agreement with a repression by glucose of the gene encoding 20αHSD. The conversion starts after 16 h when the glucose is depleted. The conversion of 17α-hydroxyprogesterone to 4-pregnene-17α,20α-diol-3-one was approximately 4 times higher after 48 h when the yeasts were cultured in the presence of galactose. These results were moreover confirmed in vitro by measuring the 20αHSD activity on an acellular extract obtained from yeasts cultured in galactose or glucose medium. The 20αHSD specific activities were respectively 0.05 and 0.75 µM/min/mg in the homogenates of cells cultured in glucose or galactose medium.

These results therefore show (i) that the 20αHSD activity is carried by the product of the yeast GCY1 and YPR1 genes, (ii) that these enzymes are soluble, and (iii) that their activity may be increased in the presence of galactose and repressed in the presence of glucose.

Construction and properties of yeasts containing a non-functional GCY1 and/or YPR1 gene With the aim of confirming that Gcy1p was responsible for the 20αHSD activity, the gene corresponding to ORF YOR120w was deleted (Knock Out) from the yeast genome. The results obtained show that the strain obtained has a highly reduced 20αHSD activity compared with the wild-type strain. Moreover, strains in which the YPR1 gene alone or in combination with GCY1 is deleted were also constructed and tested for their activity, as described below.

Construction of deficient GCY1 and/or YPR1 yeasts:

The yeasts deficient in GCY1 and/or YPR1 activity were prepared by gene disruption. More particularly:

The strain TGY170 (FY1679-28c, gcy1::LEU2) was constructed by disrupting the GCY1 gene by means of the plasmid Pgcy1::LEU2.

The strain TGY197 (FY1679-28c, gcy1::LEU2 ydr368w::URA3) was generated by additional disruption of the YDR368w gene (YPR1), according to the method described for ATF2 (Cauet et al., 1999) by means of the plasmid pTG12011.

The strains TGY195 were generated by disruption of the gene YDR368w (YPR1), according to the method described for ATF2 (Cauet et al., 1999) by means of the plasmid pTG12011.

The strains TGY194 (FY1679-28c, gcy1::URA3) were constructed by disrupting the GCY1 gene by means of the plasmid pTG12010.

The strains FY1679-28c/pTG10497 and TGY245 were constructed by means of the plasmids pTG10497 and pTG12045.

The following plasmids were used to disrupt the GCY1 and YPR1 genes: pgcy1::LEU2, pTG12010, pTG12011 (FIGS. 4-6), pTG12086 and pTG12045. The single copy plasmid pTG10497 is used for the expression of P450c21.

The plasmid pgcyl::LEU2, described by Magdolen et al., Gene 90 (1990) 105 114, contains the GCY1 gene whose coding sequence and promoter have been interrupted by the sequence encoding the LEU2 gene. More precisely, the promoter and the coding portion corresponding to the EcoRV and HincII restriction fragment were replaced by the HpaI fragment of 2.17 Kbases of the LEU2 gene. Thus the GCY1 gene was deleted for its promoter and for 306 base pairs of its coding sequence. The plasmid pgcyl::LEU2 was linearized by the restriction enzymes HindIII and BamHI, the HindIII BamHI fragment of 3.1 kb containing the disrupted gene was prepared in order to transform the strain Fy 1679-28c using the protocol described by Gietz RD et al. (Yeast 1995 Apr. 15; 11 (4) : 355-60 Studies on the transformation of intact yeast cells by the LiAc/SS-DNA/PEG procedure). The colonies were selected on a leucine-free medium. The positive colonies in this screen were then cultured in rich medium in order to carry out a bioconversion of 17OH progesterone as described in Dumas et al. (Eur J Biochem 1996 Jun. 1; 238 (2) : 495-504 11 beta-hydroxylase activity in recombinant yeast mitochondria. In vivo conversion of 11-deoxycortisol to hydrocortisone). The concentration of the substrate 17OH progesterone was 100 mg/l, the carbon source is galactose and the initial optical density was 0.1. The volume of the culture is 10 ml, the incubation was 48 hours at 30° C. After incubating for 48 hours, the positive clones were evaluated by extracting one ml of medium (with the cells) with 2 ml of dichloromethane and then analyzing the organic phase by reverse phase high performance liquid chromatography as described above (Dumas et al., 1996). The chromatograms were analyzed for the presence of 17,20-dihydroprogesterone in comparison with the purified product. During this incubation, a quantity of the order of 4 mg/l of 17,20-dihydroprogesterone, that is 4% of the substrate, appeared in the culture medium for the wild-type strain (not transformed by the disrupting fragment), whereas in some transformants, the presence of 17,20-dihydroprogesterone was only 1 mg/l. A TGY170 strain converting a low level of 17OH progesterone to 17,20OH progesterone and exhibiting identical growth to the wild-type strain was selected.

Two new plasmids pTG12010 and pTG12011 were constructed to allow the disruption of the GCY1 and YPR1 genes associated with the selection marker URA3.

The plasmid pTG12010 was constructed on a plasmid pUC19 base (Gene 1985; 33(1): 103-19 Improved M13 phage cloning vectors and host strains: nucleotide sequences of the M13mp18 and pUC19 vectors. Yanisch-Perron C, Vieira J, Messing J) while the plasmid pTG12011 was constructed on a plasmid pPOLYIII base (Lathe, R., Vilotte, J.-L. and Clark, J. A. Plasmid and bacteriophage vectors for excision of intact inserts JOURNAL Gene 57, 193-201 (1987)).

Construction of the plasmids pTG12010 and pTG12011

The disruption of the GCY1 gene by the URA3 gene in the plasmid pUC19 in order to arrive at pTG12010 was obtained by four successive PCR amplifications. On the one hand, three independent PCRs were carried out in order to obtain the 5' portion of the GCY1 gene (PCR1), the functional URA3 gene bordered by GCY1 sequences (PCR2), the 3' portion of the GCY1 gene (PCR3); the 5' and 3' portions of the GCY1 gene with the aid of the pairs OTG11285, OTG11286 and OTG11287, OTG11289, on a genomic DNA template of the strain Fy 1679-28c. The sequence of the oligonucleotides is the following: OTG11285: GATTCGGTAATCTCCGAA-CAggtaccAATTATATCAGTTATTACCCGGGA (SEQ ID NO: 1); OTG11286: AGCCATCTTTCAAAGCGGTT (SEQ ID NO: 2); OTG11287: CCGATCGAATCAAAACGAA-CAG (SEQ ID NO: 3); OTG11289: TCTAATCAGCTAG-TAAGAAC (SEQ ID NO: 4).

The URA3 gene, flanked by the GCY1 sequences (so as to obtain a deletion of a portion of the coding sequence of the GCY1 gene), was amplified with the aid of the oligonucleotides OTG11305 (aaccgctttgaaagatggctATCGA-TTTTCAATTCAATTCATCATTTTTTTTTATTCTTTT-TTT TG, (SEQ ID NO: 5) and OTG11306 (ctgttcgttttgattc-gatcgggAAGCTTGGGTAATAACTGATATAATTAAATT-GAACTC (SEQ ID NO: 6) from a linearized plasmid pTG10054 template (Degryse et al., In vivo cloning by homologous recombination in yeast using a two-plasmid-based system. Yeast. 1995 Jun. 15; 11 (7): 629-40). The conditions with respect to buffer and concentration of template and primers for the amplification are described by the producer or manufacturer of the enzyme TAQ DNA polymerase, and in particular for the enzyme elongase developed by Life Technologies. The temperature cycles are the following: a first cycle of 6' 30" to denature primer and template and then 30 cycles of 30 s at 93° C., 2 min at 54° C. and 3 min at 68° C., the last cycle is of 5 min at 72° C. The products PCR1, PCR2 and PCR3 were mixed in equimolar quantities and again amplified with the aid of the oligonucleotides OTG11285 and OTG11289 (see above). The final product PCR4, having a size of 1.9 Kbases, was then subcloned between the KpnI and BamHI restriction sites of the plasmid pUC19 in order to obtain the plasmid pTG12010. The structure of the plasmid was checked by restriction profiling and nucleotide sequencing of the ends. The cloning of pTG12010 in fact made it possible to obtain two versions of this plasmid, the version pTG12010#40 (pTG12010 clone 40) and pTG12010#36 (pTG12010 clone 36). The initial desire was to obtain the GCY1 gene interrupted by the URA3 gene bordered by the ClaI and HindIII sites respectively in 5' and in 3' of the gene. In fact, two different plasmids were obtained, pTG12010#36 and pTG12010#40. These two plasmids differ only in the presence or the absence of ClaI and HindIII sites at the ends of the URA3 gene. The plasmid pTG12010#40 possesses a HindIII restriction site at the 3' end of the URA3 gene but no ClaI site in 5'. The plasmid pTG12010#36 possesses no HindIII site at the 3' end but a ClaI site at the 5' end of the gene.

This property was used to obtain the plasmid which possesses the URA3 gene bordered by the HindIII and ClaI sites interrupting the coding sequence of GCY1.

Construction of the plasmid pTG12036.

The plasmid pTG12036 was constructed in 4 stages from pTG10802. The plasmid pTG10801 (which is the basis for the plasmid pTG10802) is a plasmid of the pUC type into which a succession of restriction sites has been inserted between two XhoI sites. This succession of sites comprises the HindIII, SnabI, ClaI and SpeI sites. Between the HindIII and ClaI sites, the HindIII ClaI cassette of pTG10470 (as described below) comprising the promoter TEF1, the human cDNA p450c21 and the PGK terminator, was inserted between the HindIII and ClaI sites of pTG10801 to give pTG10802. This plasmid was then digested with XhoI and therefore the cassette introduced is deleted in order to introduce a PCR fragment bordered by XhoI sites. This fragment of 2.5 kb was obtained from amplification by the pair of oligonucleotides OTG11844 (tttgctcgaggttacagaagggc, SEQ ID NO: 13) and OTG11845 (gattctcgagcaattggctgacta, SEQ ID NO: 14) on the plasmid pTG12010 (#40) in order to obtain a fragment bordered by XhoI sites containing the GCY1 gene interrupted by the URA3 gene bordered in 5' by a ClaI restriction site. This fragment was cloned between the XhoI sites of the plasmid pTG10802 in order to obtain the plasmid pTG12035. With the aim of introducing the missing HindIII site, the plasmid pTG12010 (#36) was used. This plasmid is essentially identical to pTG12010 (#40) but possesses a HindIII site in 3' of the URA3 gene at the limit with the GCY1 gene and does not possess a ClaI site in 5' of the URA3 gene at the junction with the GCY1 gene. Recombination is carried out in vivo in E. coli, between the NcoI BamHI fragment of 2.2 kb of pTG12010 (#36) (which carries from 5' to 3' a fragment of the URA3 gene and in 3' a fragment of the GCY1 gene) and a portion of the plasmid pTG12035, that is to say the large StuI, AflII fragment of 4.45 kb. The plasmid obtained pTG12036 possesses the GCY1 gene interrupted by the URA3 gene bordered by ClaI and HindIII sites in 5' and 3' respectively.

Construction of the plasmid pTG12086

This fragment is then replaced by the expression cassette of P450c21 carried by the ClaI, HindIII 2.33 Kb fragment of the plasmid pTG10469 (see below) in order to obtain the plasmid pTG12036.

Construction of the expression plasmids for Cytochrome P450c21.

For overexpression of this protein in yeast, two types of promoter were used, TEF1 ("transcription elongation factor1") and TDH3 ("glyceraldehyde-3phosphate dehydrogenase 3"). In all cases, the transcription terminator was the PGK terminator.

In these plasmids, the SalI, MluI fragment carries the cDNA for human P450c21.

Construction of the plasmids pTG10470 and pTG10469.

The plasmid pTG10298 was obtained by modifying pMAc21 (Expression and functional study of wild-type and mutant human cytochrome P45Oc21 in Saccharomyces cerevisiae. Wu DA, Hu MC, Chung BC DNA Cell Biol 1991 Apr; 10(3): 2019)) by KpnI, MluI digestion and introduction of the oligonucleotide OTG5868. The cDNA of this plasmid was obtained from the American Type Culture Collection under the name pc21/3c. It is the EcoRI-BamHI fragment of 1.6 Kb which served as the basis for the construction of the various plasmids. The modifications made are described in the above article and in the article (Expression of human 21-hydroxylase (P45Oc21) in bacterial and mammalian cells: A system to characterize normal and mutant enzyme, or Meng-Chun Hu and Bon-chu Chung DNA and Cell Biology 1991 Apr; 10 (3) 201-209).

In this procedure, the noncoding portion of P450c21 in the plasmid pMAc21 which contains the expression cassette for P450c21 was eliminated as well as the KpnI site which is present therein. The plasmid pTG10292 was obtained by transfer of the human c21 cDNA (SalI, MluI fragment) from the plasmid pTG10298 into the plasmid pTG10031 with the aid of the SalI and MluI sites. The plasmid pTG10475 was obtained by PCR and recombination. Indeed, starting with the plasmid pTG10292, a fragment of the human P450c21 cDNA representing approximately 250 nucleotides was amplified with the aid of the oligonucleotides OTG7410 (GGAATTC-CGTCGACAAAAATGCTGCTCCTGGGCCTGCTGC, SEQ ID NO: 15) and OTG5927 (CCTCAATGGTCCTCT-TGGAGTTCAGCACC, SEQ ID NO: 16). This fragment represents the coding sequence of the human P450c21 bordered by a SalI site and the sequence AAAA, as described in the oligonucleotide OTG7410. This fragment was digested with SalI and then ligated into the linear fragment of pTG10292 digested with SalI and then a recombination experiment was carried out in the strain BJ5183. The plasmid obtained pTG10475 carries a cDNA for P450c21 with a coding sequence identical to that of the natural cDNA unlike the plasmid pMAc21 on a fragment which is compatible with the vectors which we use in the laboratory, that is to say a fragment bordered by the SalI and MluI restriction sites. This fragment possesses the following environment around the ATG codon for initiation of translation GTCGACAAAAAT-GCTGCTCCTGGGCCTGCTGC (SEQ ID NO: 17). From this plasmid, the SalI, MluI fragment carrying the human P450c21 cDNA was transferred into the plasmid pTG10158 (Degryse et al., 1996) by conventional cloning in order to obtain the plasmid pTG10472. This same SalI MluI fragment of the plasmid pTG10472 was then transferred by recombination into the plasmid pTG10085 (Degryse et al., 1996) to give the plasmid pTG10469. This same fragment carrying the P450c21 cDNA on a SalI and MluI restriction fragment was transferred into the plasmid pTG10092 to give the plasmid pTG10470 (Degryse et al., 1996). This plasmid therefore carries the cDNA for human P450c21 under the control of the TEF1 promoter and a PGK terminator with a URA3-d selectable marker with an ATG initiation codon environment, as described above.

Construction of the plasmid pTG12086.

This plasmid serves for the integration of an expression cassette for P450c21 and for the disruption of the GCY1 gene at the same time.

This plasmid was constructed from the plasmid pTG12036 and the plasmid pTG10614.

The latter plasmid was constructed from pTG10212 (Degryse et al., Yeast 11: 629-640 (1995)) which is a yeast expression plasmid based on a TDH3 promoter, a PGK terminator and a URA3-d selectable marker.

Through homologous recombination in E. coli, the selectable marker was replaced by the selectable marker of the plasmid pTG10054 (Degryse et al., 1995); to do this, the MluI, FspI fragment of pTG10054 of 2.1 kb containing the URA3 marker flanked by recombination sequences was recombined with the large HindIII fragment of pTG10212 to give the plasmid pTG10610 which possesses the same characteristics as pTG10212 (Degryse et al., 1995) with a URA3 marker in the same orientation as pTG10054. The SalI, MluI fragment carrying the cDNA for human cytochrome P450c21 of the plasmid pTG10472 (see above) was transferred into the plasmid pTG10610 to give the plasmid pTG10614. The ClaI HindIII fragment of this plasmid containing from 5' to 3' the TDH3 promoter, the cDNA for human P450c21 bordered by SalI and MluI sites and then the PGK terminator was transferred into the plasmid pTG12036 to give the plasmid pTG12086 which therefore contains the sequence of the GCY1 gene interrupted by the TDH3 expression cassette for human cytochrome P450c21.

Construction of the plasmid pTG12045.

The unique SphI site of the plasmid pPoIyIII was destroyed by inserting the pair of complementary oligonucleotides OTG11975 (AAATCGATAACATG, SEQ ID NO: 18) and OTG11976 (TTATCGATTTCATG, SEQ ID NO: 19). The SphI site of pPOLYIII was destroyed and replaced by a ClaI site to give the plasmid pTG12040. Into the plasmid pTG12040, between the unique ClaI and EcoRI sites, there was introduced a ClaI EcoRI genomic DNA fragment corresponding to the 3' portion of 0.7 kb of the YPR1 gene obtained by amplification with the oligonucleotides OTG11981 (AT-TGATATCGATAAAAAGCACGGCGTTGAG, SEQ ID NO: 20) and OTG11982 (TCTCGGAATTCAGGTACTG-CAGCCAG, SEQ ID NO: 21) to give the plasmid pTG12041. Into this plasmid pTG12041 of 2.84 kb, the 5' portion of the YPR1 gene (0.66 kb) amplified by the oligonucleotides OTG11314 tacgctcgagACGTTGGTGTCATTGATATTCA, SEQ ID NO: 22) and OTG11980 (CAACTAAGCTTCAT-TCAAATAGATAGCCGC, SEQ ID NO: 23) from the genomic DNA of wild-type yeast was cloned in the form of an XhoI HindIII fragment between the SalI and HindIII sites of the plasmid pTG12041. The plasmid pTG12042 of 3.5 kb was obtained. This plasmid carries the YPR1 gene interrupted by the ClaI and HindIII sites. Between these sites, the cytochrome P450c21 cassette was cloned in the form of a ClaI HindIII fragment of 2.33 kb obtained from the plasmid pTG10469. The plasmid pTG12045 was thus obtained.

Construction of the plasmid pTG10497.

This plasmid is an expression plasmid with a low copy number (of the ARS CEN type), which contains an expression cassette for human cytochrome P450c21 which is found under the control of the TDH3 promoter and the PGK terminator. This plasmid was constructed from the plasmid pTG10434 which contains the URA3 selectable marker and the TEF1 promoter, the PGK terminator and a replication origin in yeast of the ARSH4/CEN6 type (Degryse et al., 1995).

This plasmid was modified so as to contain a marker LEU2 and promoter TDH3 in place of the markers URA3 and promoter TEF1, respectively. To do this, the SpeI, MluI fragment which contains the LEU2 marker bordered by recombination fragments which are the PGK terminator and a fragment of the replication origin was cloned by recombination in place of the URA3 region of the plasmid pTG10434 digested with HindIII to obtain the plasmid pTG10466. In this plasmid pTG10466, the TEF1 promoter was replaced by the TDH3 promoter by recombining in E. coli the HindIII, EcoRI fragment of pTG10212 (Degryse et al., 1995) (containing the replication origin of E. coli and the promoter and terminator TDH3 and PGK respectively) with the MluI, FspI fragment of pTG10466 which contains the LEU2 marker and the ARSCEN replication origin which are bordered by the recombination sequences; the plasmid pTG10612 was thus obtained. Between the SalI and MluI sites of this plasmid, the expression cassette TDH3: :human P450c21 cytochrome and terminator was placed to give the plasmid pTG10497.

Construction of the deficient strains

To obtain the strain lacking GCY1 activity, the strain FY 167928c was transformed according to the lithium acetate method described above by the plasmid pTG121010 linearized with the enzymes SphI and EcoRI. The transformed clones were selected on a uracil-free medium and then screened by amplification in situ with the aid of the pairs of oligonucleotides OTG11285, OTG11289 and OTG11285, OTG11306 using, as template, an extract or a preparation of yeast genomic DNA according to the conditions described above. The colonies which show PCR DNA products of the expected sizes, 1.9 Kb and 1.4 Kb respectively, were then cultured in rich medium to carry out a bioconversion of 17OH progesterone as described in Dumas et al. (Eur J Biochem 1996 Jun 1; 238(2) : 495-504 11 beta-hydroxylase activity in recombinant yeast mitochondria. In vivo conversion of 11-deoxycortisol to hydrocortisone). The substrate concentration was 100 mg/l, the carbon source was galactose and the starting optical density was 0.1. The culture volume was 10 ml, the incubation was 24 hours at 30° C. After 24 hours of incubation, the positive clones were evaluated by extracting one ml of medium (with the cells) with 2 ml of dichloromethane and then analyzing the organic phase by reverse phase high performance liquid chromatography as described above (Dumas et al., 1996). The strains TGY194 #10 and TGY194 #11 lack 20 keto reductase activity on 17OH progesterone and gave a positive signal in PCR.

The interruption of the YPR1 (YDR368w) gene by the URA3 gene in the plasmid pPOLYIII to lead to pTG12011 was obtained by 4 successive PCRs. On the one hand, three independent PCRs were carried out in order to obtain the 5' portion of the YPR1 gene (PCR 5), the functional URA3 gene bordered by YPR1 sequences (PCR 6), the 3' portion of the YPRI gene (PCR 7). The PCR 5 DNA was obtained by amplification on a genomic DNA template with the oligonucleotides OTG11314 (tacgctcgagACGTTGGTGTCAT-TGATATTCA, (SEQ ID NO: 7) and OTG11315 (CTTCAT-TCAAATAGATAGCCG, (SEQ ID NO: 8), likewise the PCR 7 DNA is obtained by amplification with the aid of the oligonucleotides OTG11316 (TATGGCTAAAAAGCACGGCTT, (SEQ ID NO: 9) and OTG11317 (cgatctcgagTTTCTCGT-TGTTCAGGTACTG, (SEQ ID NO: 10) on the same template. The URA3 gene flanked by the 5'and 3' YPR1 region was amplified with the aid of the oligonucleotides OTG11463 (CGGCTATCTATTTGAATGAAGatcgattttcaattcaattcatca-ttttttttttattctttttttg, (SEQ ID NO: 11) and OTG11464 (AACGCCGTGCTTTTTAGCCATAAGCTTgggtaataactg-atataattaaattgaactc, (SEQ ID NO: 12) on a linearized pTG10054 template as described above. The PCR 5, PCR 6 and PCR 7 products were mixed in equimolar quantities then amplified by PCR with the aid of the oligonucleotides OTG11314 and OTG11317 to give a 1.xkb product of PCR 8 as described above. This PCR 8 product was digested with the enzyme XhoI and then subcloned into the plasmid pPOLYIII digested with XhoI. The orientation of the insertion in the plasmid pPOLYIII was determined by digestion with the enzymes NcoI and EcoRI.

Strangely, the absence of a ClaI site and of an HindIII site was noted for the plasmids pTG12010 and pTG12011, respectively. The cloning junctions were checked by nucleotide sequencing.

Construction of the TGY195 strain.

The plasmid pTG12011 was digested with the enzyme XhoI, the product of digestion was then used to transform the strain Fy 1679-28c using the lithium chloride method cited above. The transformants were selected on a uracil free medium. The transformants were analysed by PCR amplification using the oligonucleotides which served for the construction of the plasmid pTG12011. The positive clones in this test were then screened by the 17OH progesterone bioconversion method described above in the presence of glucose as carbon source. A clone TGY195#4 was selected for new characterizations.

Construction of the TGY197 strain

A clone TGY195#4 exhibiting reduced 20 keto reductase activity under these conditions was selected for a new transformation with the aid of the plasmid pgcyl::LEU2 as described above for the strain Fy1679-28c. The clones capable of growing in the absence of leucine were then selected for a new bioconversion on 17OH progesterone as described above in the presence of glucose or galactose. A clone TGY197#a exhibiting reduced activity under the two bioconversion conditions was selected. Thus, the 20 keto reductase activity which was originally 12% (at 100 mg/l of substrate) was reduced to about 0.2%, that is a reduction of more than 60 fold.

Construction of the TGY245 strain

The TGY245 strain was constructed from the TGY195#4 strain. From the TGY195#4 strain, the strain TGY212#1 was first obtained followed by the strain TGY243#1 and finally the strain TGY245.

The strain TGY195#4 was transformed using both the plasmid YRP7 (1 μg) and 5 μg of plasmid pTG12045 digested with NotI. The transformed strains were selected on a tryptophan-free medium. Colonies (678 colonies) were subcultured on a tryptophan-containing medium (so as to eliminate the plasmid YRP7) and on a medium containing tryptophan and 5-fluoroorotate (5FO) to select the colonies which have lost the URA3 gene interrupting the GCY1 gene. One colony was selected from this screen, TGY212#1. This colony was subjected to a bioconversion experiment as described above with 100 μg/ml of 17OH progesterone substrate, the strain is grown in a minimum medium supplemented with necessary amino acids and uracil. This strain was capable of converting 17OH progesterone to 11-deoxycortisol with an efficiency of the order of 47% over 24 hours with a low production of 4-pregnene-17α,20α-diol-3-one under these conditions (<0.5%). Under certain conditions (defined rich medium of the Kappeli type with galactose as carbon source and starting the culture at high density: OD600 nm=5), the capacity for reducing the ketone was increased, reaching 11% of the initial substrate with a bioconversion capacity reduced to 1.5% of the initial substrate. Under these conditions, the probable presence of the GCY1 gene negatively affected the bioconversion of 17OH progesterone. We therefore decided to disrupt the GCY1 gene in order to prevent its activity.

To do this, the TGY212#1 strain was transformed with 3 µg of the plasmid pTG12010#36 linearized with the restriction enzymes SphI and EcoRI. Twenty-seven transformants were selected on a minimum medium supplemented for the auxotrophies of TGY212#1 but containing no uracil. These colonies were subjected to bioconversion tests in a minimum medium supplemented with galactose as carbon source because the latter is a known inducer of GCY1. All the TGY243 clones exhibited a capacity to convert 17OH progesterone to 11-deoxycortisol without, as a result, producing detectable quantities of 4-pregnene-17α,20α-diol-3-one. A TGY243#1 clone was selected in order to introduce in the place of the URA3 gene an expression cassette for human P450c21.

This TGY243#1 strain was transformed with the plasmid YRP7 (2 µg) and with the plasmid pTG12086 linearized with the enzyme XhoI (5 µg). The pTG12086 transforming fragment contained the coding sequence of GCY1 interrupted by an expression cassette for human P450C21 (TDH3::human cDNAP450c2I::PGK terminator). The colonies growing in the absence of tryptophan were selected. These 381 colonies were then transferred onto a medium containing tryptophan and 5-fluoroorotate. About ten colonies were then tested in a rich medium of the YPG type supplemented with tryptophan, histidine, leucine and uracil at a concentration of 50 µg/ml. The strains were then allowed to convert 170H progesterone at a concentration of 100 µg/ml starting with an OD600 nm of 0.1 for 16 hours.

Among these 10 clones, a clone TGY245#1D was chosen based on two criteria, in particular the capacity to convert 170H progesterone to 11-deoxycortisol and secondly the absence of formation of 4-pregnene-17α,20α-diol-3-one indicating the disruption of GCY1.

Property of the deficient GCY1 strains:

The results obtained show that the "Knock Out" of CGY1 eliminates the 20αHSD activity inducible by galactose. Thus, the production in vivo of 4-pregnene -17α,20α-diol-3-one from 17α-hydroxyprogesterone (100 µg/ml) was tested in a culture of wild-type strains and of TGY170 strains (gcyl-A:: LEU2), cultured either in glucose medium or in galactose medium (FIG. 3). In the case of a culture in galactose medium, a reduction of about 95% in the production of 4-pregnene-17α,20α-diol-3-one was observed for the mutant strain compared with the wild-type strain. In glucose medium, the reduction was lower, which appears to indicate that the product of the GCY1 gene comprises a 20αHSD activity which is inducible by galactose. Whatever the source of carbon used, the residual activity present in the mutant gcyll-Δ is substantially unchanged.

Properties of the deficient GCY1, YRP1 double mutant:

Given the fact that Gcylp and Yprlp were found associated with the 20αHSD activity (see above), and that Yprlp is the closest homologue of Gcylp (65% amino acid identity), a double disruption of GCY1 and of YPR1 was performed and tested for its 20αHSD type activity. The results obtained show that the strain deficient for the two genes (TGY197) was essentially free of 20αHSD activity.

More particularly, the TGY197 yeasts (gcyl::LEU2,yprl:: URA3) were generated and tested in vivo for their 20αHSD activity. The cells were cultured with either glucose or galactose as the carbon source, in the presence of 100 µg/ml of 17α-hydroxyprogesterone. After 72 h, 4-pregnene-17α,20α-diol-3-one was undetectable in the fermentation liquid, demonstrating that the inactivation of the two genes leads to a suppression of the detectable 20αHSD activity.

Substrate specificity of the wild-type and mutant strains

A series of components already described as substrates for various classes of reductases (aldose-, aldehyde- and carbonyl-reductases) was tested on wildtype homogenates and on mutant strains under various culture conditions (Table II). It was observed that Gcy1p and Ypr1P are the only aldo-keto yeast reductases which accept 17α-hydroxyprogesterone as substrate.

Gcylp appears to use all the substrates tested since in all cases, induction by galactose increases activity. In glucose medium, a basal activity was observed for all the components with the exception of 17α-hydroxyprogesterone, independently of the presence of Gcy1P and Yprlp. In galactose medium, a higher activity was observed in the mutant strains for the two aldehydes tested, although less pronounced than in the wild-type strains. This indicates that an enzyme specific for aldehydes other than Gcy1P is inducible by galactose.

In a recent report on the physiology of yeasts under osmotic stress, GCY1 was identified as being reactive. The sequencing of a peptide isolated from an *Aspergillus niger* glycerol dehydrogenase has shown homology with two yeast proteins: Gcy1P and Yprlp. The induction of GCY1 under osmotic stress (in addition to its induction by galactose) could indicate that GCY1 comprises a glycerol dehydrogenase activity, as suggested in Norbeck and Blomberg. However, such an activity has not been demonstrated up until now.

The reduction of 17α-hydroxyprogesterone to 4-pregnene-17α,20α-diol-3-one in *S. cerevisiae* is mainly due to the product of the GCY gene and, to a lesser degree, to the product of the YPR1 gene. According to the nomenclature proposed by Jez et al. (1997), these enzymes ought to be classified in the AKR1C subfamily. In mammals, HSDs, belonging to the AKR family, have been proposed for regulating the availability of steroid hormones. The physiological role of these enzymes in yeast remains unknown, since yeasts are not supposed to be capable to being exposed to steroids in a natural environment. Whatever the biological significance of such an activity in yeast, its elimination contributes to improving the production of corticosteroids from yeasts, in particular from genetically modified yeasts according to the invention.

Example of Bioconversion with Human P450c21 in Yeast in the Presence and in the Absence of GCY1 and YPR1.

With the aim of showing that the disruption of GCY1 and YPR1 is essential in order to obtain a specific bioconversion in the yeast *S. cerevisiae*, we compared the capacity for bioconversion of 17OH-progesterone of the strains Fy1679-28c/ pTG10497 (Fy/pTG10497), TGY212 #1 and TGY245#2D.

The strain Fy/pTG10497 carries the two wild-type genes GCY1 and YPR1 and the single copy plasmid of ARSCEN type ("Autonomously Replicating Sequence Centromer") for expression of human P450c21. The cDNA for human P450c21 is under the control of the TEF1 promoter in this plasmid.

The TG212#1 strain carries a copy of the expression cassette for the human P450c21 gene (TEF1::human P450c21:: PGK terminator) integrated at the YPR1 locus and possesses a wild-type copy of the GCY1 gene.

TGY245#2D does not possess copies of the YPR1 and GCY1 genes: instead, a copy of the cassette TEF1::human P450c21 and a copy of TDH3:P450c21 are integrated into each of the loci, respectively.

These strains were cultured in minimum medium with a supplement of casamino acids for 48 hours. The strains were resuspended in fresh Kappeli medium with a supplement of uracil, histidine and tryptophan in the presence of 200 mg/l of 17OH progesterone. After an incubation of 72 hours, the medium in the presence of the yeast cells was extracted and analyzed as above by reverse phase high performance liquid chromatography. The presence of 17OH progesterone, 11-deoxycortisol and 4-pregnene -17α,20α-diol-3-one was measured.

The results are presented in Table III. Each product is expressed as a percentage of the sum of all the products.

According to this experiment, it appears clearly that the disruption of GCY1 and YPR1 significantly reduces the quantity of 4-pregnene-17α,20α-diol-3-one from 7-11% to a level which is not detectable by our techniques (sensitivity of 0.5 to 1 mg/l).

REFERENCES

Amberg et al. (1995), Yeast 11, 1275-1280.
Cauet et al. (1999), Eur. J. Biochem, 261, 317-324.
Degryse et al. (1995), J. Biotech. 39, 181-187.
Degryse, E. (1996), Gene 170, 45-50.
Degryse et al. (1995), Yeast 11, 629-640.
Dumas et al. (1994), Cytochrome P450, 8th International Conference, Ed. M. C. Lechner, John Libbey Eurotext, Paris, pp. 527-530.
Dumas et al. (1996), Eur. J. Biochem. 238, 495-504.
Duport et al. (1998), Nat. Biotech. 16, 1-6.
Hanahan, D. (1983) J. Mol. Biol. 166, 557-580.
Hubacek et al. (1970), J. Mol. Biol. 50, 111-127.
Ito et al. (1983), J. Bact. 153, 163-168.
Miller et al. (1988), Endocrine Revs 9, 295-318.
Sakaki et al. (1989), DNA 8, 409-418.
Sakaki et al. (1991), Pharmacogen. 1, 86-93.
Sambrook et al. (1989), Cold Spring Harbor University Press, 2nd edition, Cold Spring Harbor.
Sherman, F. (1991), Methods Enzymol. 194, 3-21.
Thierry et al. (1995), Yeast 11, 121-135.
WU et al. (1991), Saccharomyces cerevisiae DNA Cell Biol. 10, 201-209.

TABLE I

| ORF | Name of the gene | % amino acid identity with 20αHSD |
| --- | --- | --- |
| YOR120W | GCY1 | 44 |
| YDR368W | YPR1 | 43 |
| YHR104W | — | 41 |
| YBR149W | — | 40 |
| YJR096W | — | 39 |
| YDL124W | — | 32 |

TABLE III

| Product | Fy/10497 | TGY212#1 | TGY245#2D |
| --- | --- | --- | --- |
| 17OH progesterone | 74 | 87 | 28 |
| 11-deoxycortisol | 19 | 20 | 82 |
| 4-pregnene-17α, 20α-diol-3-one | 7 | 11 | 0 |

TABLE II

| | Fy1679.28c | | TGY170 | | TGY197 | |
| --- | --- | --- | --- | --- | --- | --- |
| | glucose | galactose | glucose | galactose | glucose | galactose |
| xylose | 8 | 50 | 5 | 8 | 3 | 5 |
| methylglyoxal | 75 | 376 | 92 | 88 | 56 | 104 |
| glyceraldehyde | 32 | 1119 | 40 | 357 | 42 | 384 |
| nitrobenzaldehyde | 59 | 1117 | 69 | 334 | 50 | 395 |
| 17α-hydroxyprogesterone | 0.04 | 1.44 | 0.006 | 0.01 | nd | nd |

The activities are given in μM/min/mg protein
nd: not detected

We claim:

1. An isolated *Saccharomyces cerevisiae* yeast strain comprising an inactivating genetic modification in both the YPR1 and GCY1 genes.

2. The isolated *Saccharomyces cerevisiae* yeast strain according to claim 1, wherein at least one said gene is replaced, completely or in part, by the URA3 marker gene.

3. The isolated *Saccharomyces cerevisiae* yeast strain according to claim 1 exhibiting a reduced 20α-hydroxysteroid dehydrogenase type activity.

4. A preparation derived from an isolated *Saccharomyces cerevisiae* yeast strain comprising an inactivating genetic modification in both the YPR1 and GCY1 genes wherein said preparation is selected from the group consisting of a cellular lysate, a cellular homogenate and a culture supernatant.

5. The preparation according to claim 4 wherein at least one said gene is replaced, completely or in part, by the URA3 marker gene.

6. The preparation according to claim 4 wherein said isolated *Saccharomyces cerevisiae* yeast strain exhibits a reduced 20α-hydroxysteroid dehydrogenase type activity.

* * * * *

UNITED STATES PATENT AND TRADEMARK OFFICE
CERTIFICATE OF CORRECTION

PATENT NO.         : 7,879,592 B2
APPLICATION NO.    : 10/343993
DATED              : February 1, 2011
INVENTOR(S)        : Bruno Dumas et al.

It is certified that error appears in the above-identified patent and that said Letters Patent is hereby corrected as shown below:

On the Title page, Item [56], in column 2, under "Other Publications", line 7, delete "Accesion" and insert -- Accession --, therefor.

On the Title page, Item [56], in column 2, under "Other Publications", line 13, delete "Saccharomyeces" and insert -- Saccharomyces --, therefor.

On Title page 2, Item [56], in column 1, under "Other Publications", line 29, delete "Steroi" and insert -- Sterol --, therefor.

On Title page 2, Item [56], in column 1, under "Other Publications", line 46, delete "Smith-Lemii-Opitz" and insert -- Smith-Lemli-Opitz --, therefor.

On Title page 2, Item [56], in column 1, under "Other Publications", line 48, delete "Sacaromyces" and insert -- Saccharomyces --, therefor.

On Title page 2, Item [56], in column 2, under "Other Publications", line 2, delete "Sacaromyces ceravisiae," and insert -- Saccharomyces cerevisiae, --, therefor.

On Title page 2, Item [56], in column 2, under "Other Publications", line 6, delete "Chemotheray," and insert -- Chemotherapy, --, therefor.

On Title page 2, Item [56], in column 2, under "Other Publications", line 27, delete "Smith-Lemil-Optiz" and insert -- Smith-Lemli-Opitz --, therefor.

On Title page 2, Item [56], in column 2, under "Other Publications", line 50, delete "csevisiae" and insert -- cerevisiae --, therefor.

On Title page 2, Item [56], in column 2, under "Other Publications", line 53, delete "Smith-Lemil-Optiz" and insert -- Smith-Lemli-Opitz --, therefor.

Signed and Sealed this
Seventeenth Day of April, 2012

David J. Kappos
*Director of the United States Patent and Trademark Office*

CERTIFICATE OF CORRECTION (continued)
U.S. Pat. No. 7,879,592 B2

On Title page 2, Item [56], in column 2, under "Other Publications", line 5, delete "Adrendoxin" and insert -- Adrenodoxin --, therefor.

On Title page 3, Item [56], in column 2, under "Other Publications", line 14, delete "(Arhlp)" and insert -- (Arhip) --, therefor.

On Title page 3, Item [56], in column 2, under "Other Publications", line 23, delete "Cervisiae" and insert -- Cerevisiae --, therefor.

On Title page 3, Item [56], in column 2, under "Other Publications", line 33, delete "Hydroxlase" and insert -- Hydroxylase --, therefor.

On Title page 3, Item [56], in column 2, under "Other Publications", line 43, delete "Esterificatio" and insert -- Esterification --, therefor.

In column 12, line 39, delete "pPolylll" and insert -- pPolyIII --, therefor.

In column 12, line 54, before "tacgctcgag" insert -- ( --.

In column 13, line 10, delete "MluI" and insert -- MIuI --, therefor.

In column 13, line 24, delete "MluI" and insert -- MIuI --, therefor.

In column 13, line 52, delete "lack" and insert -- lacked --, therefor.

In column 13, line 60, delete "YPRI" and insert -- YPR1 --, therefor.

In column 14, line 14, delete "Xhol." and insert -- XhoI. --, therefor.

In column 14, line 23, delete "Xhol," and insert -- XhoI, --, therefor.

In column 14, line 43, delete "mg/I" and insert -- mg/l --, therefor.

In column 14, line 53, delete "Notl." and insert -- NotI. --, therefor.

In column 15, line 25, delete "Xhol" and insert -- XhoI --, therefor.

In column 15, line 27, delete "P450C21" and insert -- P450c21 --, therefor.

In column 15, line 28, delete "cDNAP450c2I" and insert -- cDNAP450c21 --, therefor.

In column 15, line 57, delete "gcyll-Δ" and insert -- gcyl1-Δ --, therefor.

In column 16, line 60, delete "Centromer")" and insert -- Centromere") --, therefor.

In column 17, line 8, delete "mg/I" and insert -- mg/l --, therefor.

SEQUENCE LISTING

```
<160> NUMBER OF SEQ ID NOS: 23

<210> SEQ ID NO 1
<211> LENGTH: 50
<212> TYPE: DNA
<213> ORGANISM: Artificial sequence
<220> FEATURE:
<223> OTHER INFORMATION: Artificial sequence description:
      oligonucleotide

<400> SEQUENCE: 1
```
gattcggtaa tctccgaaca ggtaccaatt atatcagtta ttacccggga                50

<210> SEQ ID NO 2
<211> LENGTH: 20
<212> TYPE: DNA
<213> ORGANISM: Artificial sequence
<220> FEATURE:
<223> OTHER INFORMATION: Artificial sequence description:
      oligonucleotide

<400> SEQUENCE: 2
agccatcttt caaagcggtt                                                 20

<210> SEQ ID NO 3
<211> LENGTH: 22
<212> TYPE: DNA
<213> ORGANISM: Artificial sequence
<220> FEATURE:
<223> OTHER INFORMATION: Artificial sequence description:
      oligonucleotide

<400> SEQUENCE: 3
ccgatcgaat caaaacgaac ag                                              22

<210> SEQ ID NO 4
<211> LENGTH: 20
<212> TYPE: DNA
<213> ORGANISM: Artificial sequence
<220> FEATURE:
<223> OTHER INFORMATION: Artificial sequence description:
      oligonucleotide

<400> SEQUENCE: 4
tctaatcagc tagtaagaac                                                 20

<210> SEQ ID NO 5
<211> LENGTH: 67
<212> TYPE: DNA
<213> ORGANISM: Artificial sequence
<220> FEATURE:
<223> OTHER INFORMATION: Artificial sequence description:
      oligonucleotide

<400> SEQUENCE: 5
aaccgctttg aaagatggct atcgattttc aattcaattc atcattttt ttttattctt     60 tttttg                                                                67

<210> SEQ ID NO 6
<211> LENGTH: 60
<212> TYPE: DNA
<213> ORGANISM: Artificial sequence
<220> FEATURE:
<223> OTHER INFORMATION: Artificial sequence description:
      oligonucleotide

<400> SEQUENCE: 6
ctgttcgttt tgattcgatc gggaagcttg ggtaataact gatataatta aattgaactc     60

<210> SEQ ID NO 7
<211> LENGTH: 32
<212> TYPE: DNA
<213> ORGANISM: Artificial sequence
<220> FEATURE:
<223> OTHER INFORMATION: Artificial sequence description:
      oligonucleotide

<400> SEQUENCE: 7

-continued

```
tacgctcgag acgttggtgt cattgatatt ca                              32

<210> SEQ ID NO 8
<211> LENGTH: 21
<212> TYPE: DNA
<213> ORGANISM: Artificial sequence
<220> FEATURE:
<223> OTHER INFORMATION: Artificial sequence description:
      oligonucleotide

<400> SEQUENCE: 8
cttcattcaa atagatagcc g                                          21

<210> SEQ ID NO 9
<211> LENGTH: 22
<212> TYPE: DNA
<213> ORGANISM: Artificial sequence
<220> FEATURE:
<223> OTHER INFORMATION: Artificial sequence description:
      oligonucleotide

<400> SEQUENCE: 9
tatggctaaa aagcacggcg tt                                         22

<210> SEQ ID NO 10
<211> LENGTH: 31
<212> TYPE: DNA
<213> ORGANISM: Artificial sequence
<220> FEATURE:
<223> OTHER INFORMATION: Artificial sequence description:
      oligonucleotide

<400> SEQUENCE: 10
cgatctcgag tttctcgttg ttcaggtact g                               31

<210> SEQ ID NO 11
<211> LENGTH: 68
<212> TYPE: DNA
<213> ORGANISM: Artificial sequence
<220> FEATURE:
<223> OTHER INFORMATION: Artificial sequence description:
      oligonucleotide

<400> SEQUENCE: 11
cggctatcta tttgaatgaa gatcgatttt caattcaatt catcattttt tttttattct    60
tttttttg                                                            68

<210> SEQ ID NO 12
<211> LENGTH: 58
<212> TYPE: DNA
<213> ORGANISM: Artificial sequence
<220> FEATURE:
<223> OTHER INFORMATION: Artificial sequence description:
      oligonucleotide

<400> SEQUENCE: 12
aacgccgtgc tttttagcca taagcttggg taataactga tataattaaa ttgaactc     58

<210> SEQ ID NO 13
<211> LENGTH: 23
<212> TYPE: DNA
<213> ORGANISM: Artificial sequence
<220> FEATURE:
<223> OTHER INFORMATION: Artificial sequence description:
      oligonucleotide
```

<400> SEQUENCE: 13
tttgctcgag gttacagaag ggc                                    23

<210> SEQ ID NO 14
<211> LENGTH: 24
<212> TYPE: DNA
<213> ORGANISM: Artificial sequence
<220> FEATURE:
<223> OTHER INFORMATION: Artificial sequence description:
      oligonucleotide

<400> SEQUENCE: 14
gattctcgag caattggctg acta                                   24

<210> SEQ ID NO 15
<211> LENGTH: 40
<212> TYPE: DNA
<213> ORGANISM: Artificial sequence
<220> FEATURE:
<223> OTHER INFORMATION: Artificial sequence description:
      oligonucleotide

<400> SEQUENCE: 15
ggaattccgt cgacaaaaat gctgctcctg ggcctgctgc                  40

<210> SEQ ID NO 16
<211> LENGTH: 29
<212> TYPE: DNA
<213> ORGANISM: Artificial sequence
<220> FEATURE:
<223> OTHER INFORMATION: Artificial sequence description:
      oligonucleotide

<400> SEQUENCE: 16
cctcaatggt cctcttggag ttcagcacc                              29

<210> SEQ ID NO 17
<211> LENGTH: 32
<212> TYPE: DNA
<213> ORGANISM: Artificial sequence
<220> FEATURE:
<223> OTHER INFORMATION: Artificial sequence description:
      oligonucleotide

<400> SEQUENCE: 17
gtcgacaaaa atgctgctcc tgggcctgct gc                          32

<210> SEQ ID NO 18
<211> LENGTH: 14
<212> TYPE: DNA
<213> ORGANISM: Artificial sequence
<220> FEATURE:
<223> OTHER INFORMATION: Artificial sequence description:
      oligonucleotide

<400> SEQUENCE: 18
aaatcgataa catg                                              14

<210> SEQ ID NO 19
<211> LENGTH: 14
<212> TYPE: DNA
<213> ORGANISM: Artificial sequence
<220> FEATURE:
<223> OTHER INFORMATION: Artificial sequence description:
      oligonucleotide

<400> SEQUENCE: 19

```
ttatcgattt catg                                                       14

<210> SEQ ID NO 20
<211> LENGTH: 30
<212> TYPE: DNA
<213> ORGANISM: Artificial sequence
<220> FEATURE:
<223> OTHER INFORMATION: Artificial sequence description:
      oligonucleotide

<400> SEQUENCE: 20
attgatatcg ataaaaagca cggcgttgag                                      30

<210> SEQ ID NO 21
<211> LENGTH: 26
<212> TYPE: DNA
<213> ORGANISM: Artificial sequence
<220> FEATURE:
<223> OTHER INFORMATION: Artificial sequence description:
      oligonucleotide

<400> SEQUENCE: 21
tctcggaatt caggtactgc agccag                                          26

<210> SEQ ID NO 22
<211> LENGTH: 32
<212> TYPE: DNA
<213> ORGANISM: Artificial sequence
<220> FEATURE:
<223> OTHER INFORMATION: Artificial sequence description:
      oligonucleotide

<400> SEQUENCE: 22
tacgctcgag acgttggtgt cattgatatt ca                                   32

<210> SEQ ID NO 23
<211> LENGTH: 30
<212> TYPE: DNA
<213> ORGANISM: Artificial sequence
<220> FEATURE:
<223> OTHER INFORMATION: Artificial sequence description:
      oligonucleotide

<400> SEQUENCE: 23
caactaagct tcattcaaat agatagccgc                                      30
```